US 9,988,608 B1

United States Patent
Crown et al.

(10) Patent No.: US 9,988,608 B1
(45) Date of Patent: Jun. 5, 2018

(54) METHODS OF EXPANDING BACTERIOPHAGE HOST-RANGE AND BACTERIOPHAGE PRODUCED BY THE METHODS

(71) Applicant: Sandia Corporation, Albuquerque, NM (US)

(72) Inventors: Kevin K. Crown, Albuquerque, NM (US); Joshua Santarpia, Albuquerque, NM (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 8 days.

(21) Appl. No.: 14/883,366

(22) Filed: Oct. 14, 2015

Related U.S. Application Data

(60) Provisional application No. 62/063,873, filed on Oct. 14, 2014.

(51) Int. Cl.
*C12N 7/00* (2006.01)
*C12Q 1/02* (2006.01)

(52) U.S. Cl.
CPC .............. *C12N 7/00* (2013.01); *C12Q 1/02* (2013.01); *C12N 2795/00051* (2013.01)

(58) Field of Classification Search
None
See application file for complete search history.

(56) References Cited

U.S. PATENT DOCUMENTS

2003/0180319 A1* 9/2003 Rapson .................. A01N 63/00
506/1

OTHER PUBLICATIONS

Domingo-Calap et al. Nucleoside analogue mutagenesis of a single-stranded DNA virus: evolution and resistance. J Virol. Sep. 2012;86(18):9640-6.*
Tetart, et al., "Bacteriophage T4 Host Range is Expanded by Duplications of a Small Domain of the Tail Fiber Adhesin", J. Mol. Biol. (1996) 258, 726-731.
Tetart, et al., "Genome Plasticity in the Distal Tail Fiber Locus of the T-even Bacteriophage: Recombination between Conserved Motifs Swaps Adhesin Specificity", Article No. mb982047, J. Mol. Biol. (1998) 282, 543±556.
Thiel, "Old dogma, new tricks—21st Century phage therapy", Nature Biotechnology, vol. 22, No. 1, Jan. 2004, pp. 31-36.
Yoichi, et al., "Alteration of tail fiber protein gp38 enables T2 phage to infect *Escherichia coli* O157:H7", Journal of Biotechnology 115 (2005) 101-107.
Coffey, et al., "Arbovirus evolution in vivo is constrained by host alternation", PNAS, May 13, 2008, vol. 105, No. 19, 6970-6975.
Domingo, et al., "Basic Concepts in RNA Virus Evolution", The FASEB Journal, vol. 10, Jun. 1996, 859-864.
Riede, et al., "DNA Sequence of Genes 38 Encoding a Receptor-recognizing Protein of Bacteriophages T2, K3 and of K3 Host Range Mutants", J. Mol. Biol. (1987) 194, 31-39.
Clokie MRJ & Kropinski AM (Eds.), "Bacteriophages: methods and protocols—vol. 1: isolation, characterization, and interactions," Humana Press (New York, NY), 2009 (313 pp.).
Crown KK, "Bacteriophage host-range expansion to include two strains of *Clostridium sporogenes*," M.S. thesis for Biology at the University of New Mexico, 2014 (46 pp.).
Kiritani K et al., "Numerical taxonomy of *Clostridium botulinum* and *Clostridium sporogenes* strains, and their susceptibilities to induced lysins and to mitomycin C," *Japan J. Microbiol.* 973;17(5):361-72.
Levine M, "Effect of mitomycin C on interactions between temperate phages and bacteria," *Virology* 1961;13:493-9.
Mayer MJ et al., "Genomic sequence of bacteriophage ATCC 8074-B1 and activity of its endolysin and engineered variants against *Clostridium sporogenes,*" *Appl. Environ. Microbiol.* May 2012;78(10):3685-92.

* cited by examiner

*Primary Examiner* — Michelle S Horning

(57) ABSTRACT

A method of producing novel bacteriophages with expanded host-range and bacteriophages with expanded host ranges are disclosed. The method produces mutant phage strains which are infectious to a second host and can be more infectious to their natural host than in their natural state. The method includes repeatedly passaging a selected phage strain into bacterial cultures that contain varied ratios of its natural host bacterial strain with a bacterial strain that the phage of interest is unable to infect; the target-host. After each passage the resulting phage are purified and screened for activity against the target-host via double-overlay assays. When mutant phages that are shown to infect the target-host are discovered, they are further propagated in culture that contains only the target-host to produce a stock of the resulting mutant phage.

13 Claims, 25 Drawing Sheets

Step 1: Ensure Phage infects one bacterial host but not the target host

*Clostridium sporogenes* ATCC 17886 and 7955
Bacteriophage ATCC 17886-B1/B3

Assay Used to Determine Phage Infectivity

*(Plaque Assay developed by Renato Dulbecco 1952)*

Base Layer
1.5% Agar Medium

Infection
300 µL Bacterial Culture
+ 100 µL Phage Sample

Top Layer
(4 mL) 0.7% Agar Medium
+ 400 µL Infected Culture

Figure 3

Step 2: Phage Passaging

2) Culture Host and Target-Host independently (10mL/ea)

Establishing Co-Cultures for Infection

3) Combine cultures in specified ratios

-MC Co-culture Infections Against Cs-7955

| | 100% 17886 (0% 7955) | 90% 17886 (10% 7955) | 50% 17886 (50% 7955) | 10% 17886 (90% 7955) | 0% 17886 (100% 7955) |
|---|---|---|---|---|---|
| B1 x 1 | 12 | 0 | 0 | 0 | 0 |
| B1 x 2 | 0 | 0 | 0 | 0 | 0 |
| B1 x 3 | 1 | 0 | 0 | 2 | 0 |
| B1 x 4 | 0 | 0 | 0 | 0 | 0 |
| B1 x 5 | 0 | 0 | 0 | 0 | 0 |
| B1 x 6 | 0 | 0 | 0 | 0 | 0 |
| B3 x 1 | 0 | 0 | 0 | 0 | 0 |
| B3 x 2 | 23 | 21 | 0 | 0 | 0 |
| B3 x 3 | 0 | 0 | 0 | 42 | 17 |
| B3 x 4 | TNTC | TNTC | 0 | 0 | 0 |
| B3 x 5 | 0 | 0 | No Lawn | 3 | 0 |
| B3 x 6 | 0 | 0 | No Lawn | 0 | 0 |

Figure 22

+MC Co-culture Infections Against Cs-7955

| | 100% 17886 (0% 7955) | 90% 17886 (10% 7955) | 50% 17886 (50% 7955) | 10% 17886 (90% 7955) | 0% 17886 (100% 7955) |
|---|---|---|---|---|---|
| B1 x 1 | 0 | 0 | 1 | 1 | 0 |
| B1 x 2 | 0 | 0 | 0 | 0 | 0 |
| B1 x 3 | 0 | 0 | 1 | 0 | 0 |
| B1 x 4 | 0 | 0 | 0 | 0 | 0 |
| B1 x 5 | 0 | 0 | 0 | 0 | 0 |
| B1 x 6 | TNTC | 0 | 3 | 0 | 0 |
| B3 x 1 | 10 | 26 | 1 | 0 | 0 |
| B3 x 2 | 0 | 5 | 0 | 0 | 0 |
| B3 x 3 | 2 | 6 | 0 | 0 | 0 |
| B3 x 4 | 4 | 16 | 0 | 0 | 0 |
| B3 x 5 | 1 | 27 | 0 | 1 | 0 |
| B3 x 6 | TNTC | TNTC | 0 | 0 | 0 |

Figure 23

| -MC | | +MC | | |
|---|---|---|---|---|
| B1 | B3 | B1 | B3 | |
| B1x1 100% | B3x2 100% | B1x1 50% | B3x1 100% | B3x4 90% |
| B1x3 100% | B3x2 90% | B1x1 10% | B3x1 90% | B3x5 100% |
| B1x3 10% | B3x3 10% | B1x3 50% | B3x1 50% | B3x5 90% |
| | B3x3 0% | B1x6 100% | B3x2 90% | B3x5 10% |
| | B3x4 100% | B1x6 50% | B3x3 100% | B3x6 100% |
| | B3x4 90% | | B3x3 90% | B3x6 90% |
| | B3x5 10% | | B3x4 100% | |

Figure 24

| Total RNA Present | B1 | B3 |
|---|---|---|
| Before RNAse Treatment | 28.6ng/μL | 18.1 ng/μL |
| After RNAse Treatment | <20ng/mL | <20ng/mL |
| After Genome Isolation | <20ng/mL | <20ng/mL |

| Total dsDNA Present | | |
|---|---|---|
| Before DNAse Treatment | 3.69 ng/μL | 5.16 ng/μL |
| After DNAse Treatment | 1.06 ng/μL | 3.52 ng/μL |
| After Genome Isolation | 0.186 ng/μL | 0.171 ng/μL |
| Miniprep from crude sample (no other treatment) | 4.36 ng/μL | 6.28 ng/μL |

| Total ssDNA Present | | |
|---|---|---|
| Before DNAse Treatment | 10.3 ng/μL | 6.64 ng/μL |
| After DNAse Treatment | 10.4 ng/μL | 3.78 ng/mL |
| After Genome Isolation | 0.572 ng/μL | 0.564 ng/μL |
| Miniprep from crude sample (no other treatment) | 16.1 ng/μL | 32.4 ng/μL |

Figure 25

| Total dsDNA Present | ng/µl |
|---|---|
| Before DNAse Treatment | 3.32 |
| After DNAse Treatment | 1.44 |
| After Genome Isolation | 1.49 |
| After T7 Endo I Digest (digests dsDNA) | 0.85 |
| After Exo T Digest (digests ssDNA) | 1.54 |

| Total ssDNA Present ng/µl | ng/µl |
|---|---|
| Before DNAse Treatment | 28.35 |
| After DNAse Treatment | 4.27 |
| After Genome Isolation | 9.77 |
| After T7 Endo I Digest (digests dsDNA) | 10.03 |
| After Exo T Digest (digests ssDNA) | 5.5 |

Figure 26

METHODS OF EXPANDING BACTERIOPHAGE HOST-RANGE AND BACTERIOPHAGE PRODUCED BY THE METHODS

CROSS-REFERENCE TO RELATED APPLICATIONS

This application claims benefit of U.S. Provisional Patent Application No. 62/063,873, "METHOD OF EXPANDING BACTERIOPHAGE HOST-RANGE AND BACTERIOPHAGE PRODUCED BY THE METHOD," filed Oct. 14, 2014, the content of which is incorporated by reference herein in its entirety.

STATEMENT CONCERNING FEDERALLY SPONSORED RESEARCH

This invention was developed under Contract DE-AC04-94AL85000 between Sandia Corporation and the United States Department of Energy. The U.S. Government has certain rights in this invention.

FIELD OF THE INVENTION

The present invention is directed to methods of expanding the host-range of existing bacteriophages and the resulting mutated bacteriophages with expanded host-range.

BACKGROUND OF THE INVENTION

Antibiotics have found their way into mainstream human healthcare, veterinary medicine, agriculture, and in many prophylactic uses such as in soaps and sprays since their development in the 1940's. As a result of the ubiquitous use of antibiotics, antibiotic resistant strains of bacteria have evolved that are becoming increasingly difficult to treat. For each bacteria species, sub-species, and even bacterial serotype in existence, a specific bacteriophage exists that infects it. A bacteriophage (phage) is a virus that infects and replicates within a bacterium. The term is derived from "bacteria" and the Greek (phagein), "to devour". Phages are composed of proteins that encapsulate a DNA or RNA genome, and may have relatively simple or elaborate structures.

Phage applications have recently been approved by the Food and Drug Administration (FDA) to be used in the American food industry to eliminate the presence of specific bacteria such as infectious *Listeria, Salmonella*, and *E. coli* from ready-to-eat meats and prepackaged salads as well as to ward off competing bacterial organisms which may arise within the active cultures in various yogurts. Viruses are known to undergo mutation very quickly and even retain mutations which cause them to infect bacteria other than their established host.

Phages have been shown to be effective at neutralizing in vivo bacterial infections as well as an effective prophylactic application to items that may encounter bacterial contamination. Phage, however, are very host specific so searching for, isolating, and propagating phage that are specific to a particular "problem" bacterial strain or serotype can be challenging. That notwithstanding, the current problem with using phage to eliminate (or prevent) infections and/or bacterial contamination is that phage are often too specific to each type of bacterium to be useful against real-world infection or contamination.

This problem has been answered in current industry by creating "phage cocktails" which contain several different variants of phages to combat a single, specific bacterial strain. The Eliava Institute, for example has accumulated an extensive collection of different phages that they use in cocktails to treat bacterial infections in human patients in vivo. Other companies such as Micreos and Intralytix, Inc. have patented phage cocktails targeting *Listeria, Salmonella*, and *E. coli* which are currently being sprayed on ready-to-eat foods such as prepackage salads, lunch meats, chicken, and fish. The same phage cocktails are also being used to clean surface contamination in food processing plants as well as on certain crops such as tomatoes and chilies. In addition, using phage applications on crops and livestock falls within the "organic" status for US food production.

What is needed are methods of producing bacteriophages with expanded host-range and bacteriophages with expanded host-ranges that solve the problems and limitations of the prior art.

BRIEF DESCRIPTION OF THE DRAWINGS

FIG. 2 illustrates an embodiment of the first step of a method according to an embodiment of the present disclosure.

FIG. 3 illustrates an embodiment of the first step of a method according to an embodiment of the present disclosure.

FIG. 22 shows Table 1, which shows the results of plaque assays using 100% target-host to screen for mutants contained in a sample taken from the product of each phage passage into cultures containing no Mitomycin C. *Too Numerous To Count (TNTC).

FIG. 23 shows Table 2, which shows the results of plaque assays using 100% target-host to screen for mutants contained in a sample taken from the product of each phage passage into cultures containing 1 μg/ml Mitomycin C. *Too Numerous To Count (TNTC).

FIG. 24 shows Table 3, which shows co-culture infections resulting in mutant plaque forming units.

FIG. 25 shows Table 4, which shows B1/B3 phage genome determination/isolation.

FIG. 26 shows Table 5, which shows B3 phage genome determination (averaged standardized values).

Wherever possible, the same reference numbers will be used throughout the drawings to represent the same parts.

SUMMARY OF THE INVENTION

Figure 1:
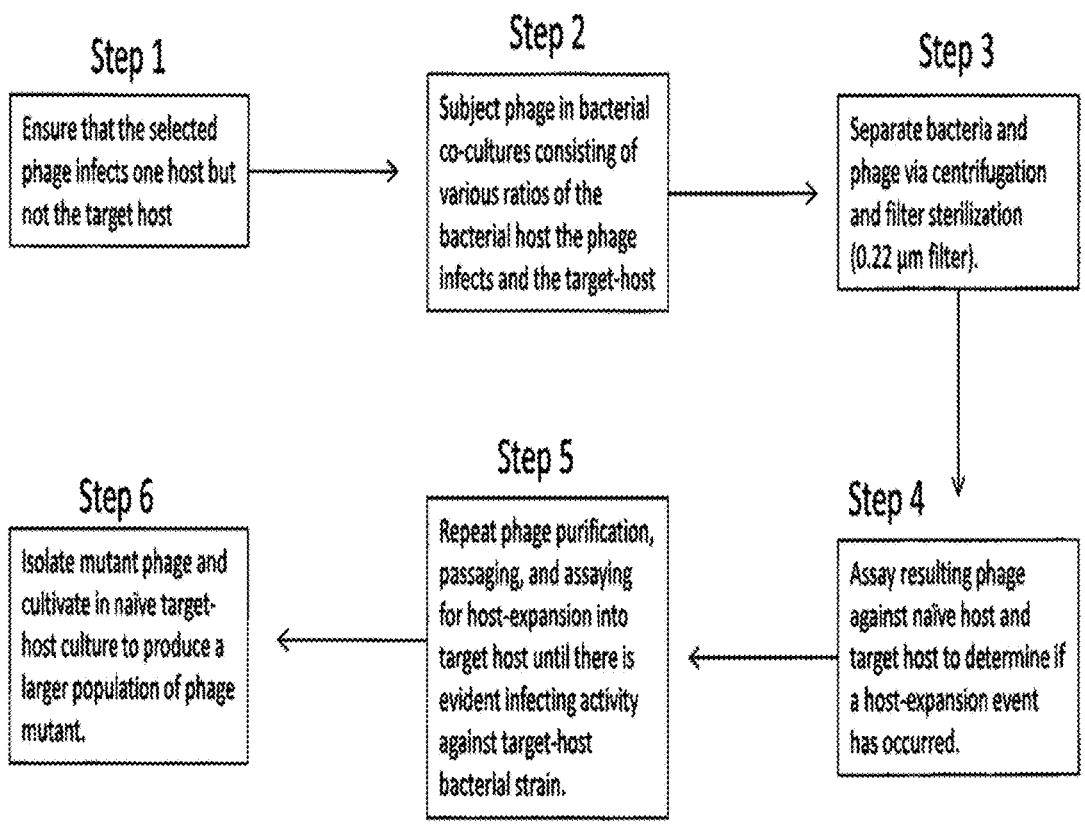
FIG. 1 is a flowchart of a method according to an embodiment of the present disclosure.

The present disclosure is directed methods of producing novel bacteriophage (phage) strains with expanded host-ranges and the resulting phages.

The present disclosure is further directed to methods that propagate known phage strains in such a way as to expand their host-range to specific bacteria of interest. In this way, instead of searching the environment for phage strains that infect bacteria of interest, phage types can be made to fit the problem at hand. Mutated phage strains can then be used as a tool, alone or in conjunction with antibiotics, to fight infections or as prophylaxis.

The present disclosure is further directed to methods of producing novel bacteriophages with expanded host-range and bacteriophages with expanded host ranges are disclosed. The method produces mutant phage strains which are infectious to a second host and can be more infectious to their natural host than in their natural state. The method includes repeatedly passaging a selected phage strain into bacterial cultures that contain varied ratios of its natural host bacterial strain with a bacterial strain that the phage of interest is unable to infect; the target-host. After each passage the resulting phage are purified and screened for activity against the target-host via double-overlay assays. When mutant phages that are shown to infect the target-host are discovered, they are further propagated in culture that contains only the target-host to produce a stock of the resulting mutant phage.

The present disclosure is further directed to a method of producing bacteriophages with expanded host-range by the following steps: determine that a selected phage strain infects a host bacterial strain and not a target-host bacterial strain; subject phage in bacterial co-cultures consisting of various ratios of the bacterial host the phage infects and the target-host; separate bacterial and phage; assay resulting phage against naïve host and target-host to determine if a host-expansion event has occurred; repeat phage purification, passaging, and assaying for host-expansion into target-host until there is evident infecting activity against target-host bacterial strain; and isolate mutant phage and cultivate in naïve target-hosts culture to produce a population of phage mutant.

The present disclosure is further directed to a method of forming a mutant phage cocktail by combining one or more populations of mutant phages. Multiple mutant phages can be produced independently that each infect one desired bacterial strain. Each mutant phage may carry a mutation that affects its mode of infection that is different from one another. By combining multiple mutant phages into a cocktail, a culture of one bacterial strain will be infected through several modes of infection making it more difficult for the bacterial culture to mount a defense against infection.

The present disclosure is also directed to forming a cocktail of phage types intended to infect several different bacterial strains residing in a culture or infection. Several mutant phages that infect one bacterial strain combined with several mutant phages that infect another bacterial strain.

An advantage of the present invention is to broaden the use of currently known phage strains to fight more diverse bacterial variants as an alternative to using antibiotics in human health and industry.

Other features and advantages of the present invention will be apparent from the following more detailed description of the preferred embodiment, taken in conjunction with the accompanying drawings which illustrate, by way of example, the principles of the invention.

DESCRIPTION OF THE INVENTION

The present disclosure is directed to methods of producing bacteriophages (phages) with expanded host-range, and the phage types produced by the disclosed methods. The disclosed process produces mutant phage strains which are more infectious to their natural host than in their natural state. In an embodiment the disclosed phages can be infectious to a second host.

The present disclosure is further directed to methods by which directed host-expansion events can be arranged yielding phage mutants that are lytic to more than one bacterial host, and to the bacteriophages produced by those methods. In an embodiment, one phage is placed in culture with its host and the bacterial strain targeted for it to infect, the "target-host". This was done with several ratios of the two bacterial strains and then passaged the phage six times, each time under the same co-culture condition. This was done with the B1 phage B3 phage (see Example below).

In an embodiment, sets of co-cultures, each containing varied ratios of the bacterial host of a selected phage serotype, and a pre-determined target-host organism are formed. After incubation the phage from each co-culture are purified and put into fresh co-cultures of the same ratio, repeating the first infection, for a total of six times, or "passages". Samples of each passage were screened against the target-host to seek out mutated phages that have expanded their host range. Many random successful mutations occurred, some of which, produced mutant phages that have been successfully propagated in larger volumes, "expanded" in the target-host. The same battery of experiments were performed with the addition of a mutagen, and yielded mutants as well. The infectivity against the original host and the target-host were then compared between the phage mutants obtained from the environments that contained no mutagen and that of the mutants obtained from the environments where the mutagen was present. While the infectivity of the mutant phages against the original host suffered no or negligible loss, the infectivity against the target-host was shown to be 16-30 k fold more infective than those mutants obtained under null mutagen conditions. Additionally, the data show that the infectivity of these phages can increase in their activity toward the original host making them more lytic and effective bacterial infecting agents. This method can be used to enhance the infection efficiency of bacteriophage against its current host as well as make novel phage mutants that are more versatile by expanding the bacterial strains that they attack.

The pre-selected phages are cultivated in such a way that they are able to infect several different variants of bacteria. In an embodiment, the pre-selected phages may be used to form a cocktail of host-expanded mutant phages to combat more diverse bacterial variants with higher efficacy.

This disclosure is further directed to methods of bacteriophage host-range expansion that can be used as a tool to produce novel phage strains and phage cocktails, as well as to improve existing phage cocktails currently used in human health and industry. It is shown herein that bacteriophage genomes can incur many random mutations during replication and that it is possible to detect and capture desired mutations. Further, by adding a small concentration of a mutagen at the onset of culture infection, more mutations can be induced thereby increasing the overall yield of the desired stable mutations which can be stably propagated into large populations. These techniques may be useful in creating efficacious novel phages for use in commercial industry and in human health. Phages created under these mutagenic conditions have greater lytic efficacy toward both their natural and target-hosts. Using these methods, the lytic activity of known phage may be improved on their natural host and expanded into new hosts.

The present disclosure is further directed to methods by which directed host-expansion events can be arranged yielding phage mutants that are lytic to more than one bacterial host. The methods include the following steps as shown in FIG. 1.

Step 1:

Ensure that the selected phage productively infects a bacterial host but does not infect the target bacterial host that is desired for the phage to infect and propagate in. This is done by using the double-overlay assay method. This step is illustrated by FIGS. 2 and 3.

Double-Overlay Assay Method:

A suitable growth medium for the host and/or target-host organisms is made with 1.2-1.5% agar, poured into sterile petri dishes, and allowed to solidify to create the "base layer". 300 µL of bacterial culture at mid-log is mixed with 100 µL of phage and incubated at RT while rocking for 15-20 minutes. The infected culture is then mixed with 4 mL of molten (50-55° C.) medium suitable for the bacteria being grown, made with 0.7-1.0% agar and poured over the top of the base agar layer in the petri dish. The "top layer" is allowed to cool to RT and solidify and is then incubated for 12-15 hours under optimal growth conditions for the bacterial strain being cultured. This step is illustrated by FIG. 3.

A double-overlay assay is performed using the phage of interest and a bacterial host that it infects along with a separate assay that contains the phage of interest and the target-host. This demonstrates that the starting phage population does, in fact, infect one bacterial host but not the other.

Figure 4:
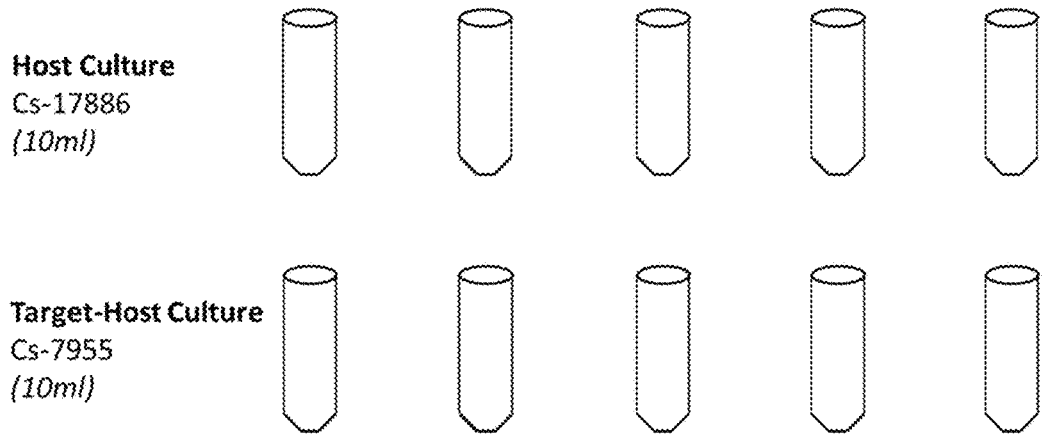
FIG. 4 illustrates an embodiment of the second step of a method according to an embodiment of the present disclosure.
Figure 5:
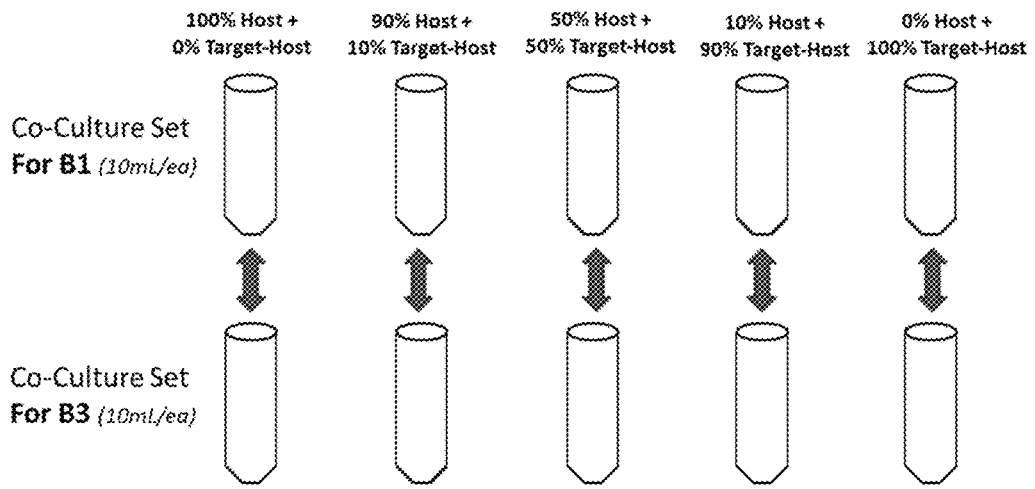
FIG. 5 illustrates an embodiment of the second step of a method according to an embodiment of the present disclosure.
Figure 6:
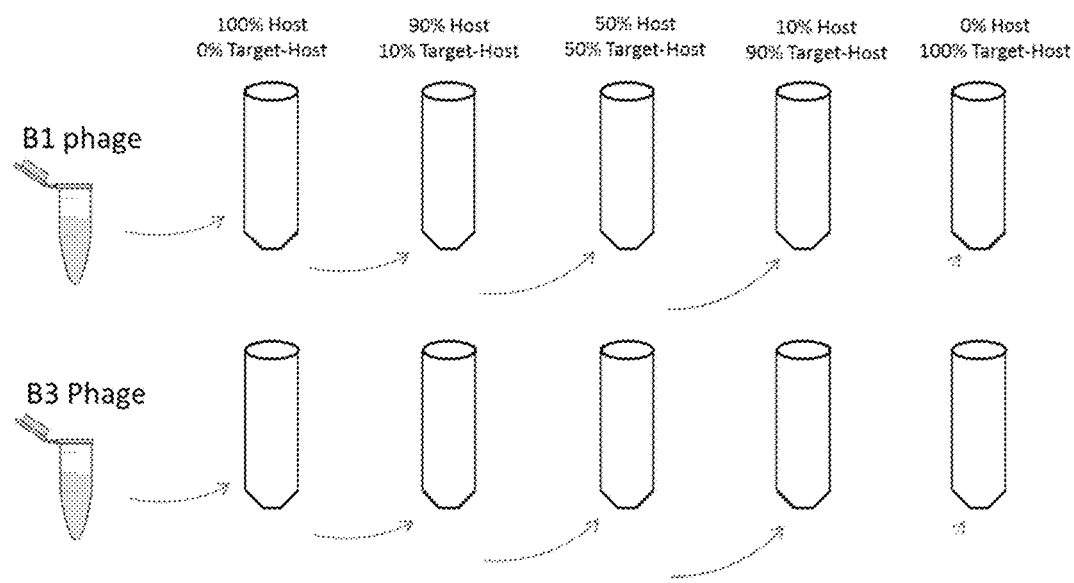
FIG. 6 illustrates an embodiment of the second step of a method according to an embodiment of the present disclosure.

Step 2:

After separately cultivating volumes of the host and target-host bacterial strains that have never been in the presence of the phage of interest, the bacterial cultures are combined in various ratios to one another to create a series of co-cultures. i.e. co-cultures may contain 10% of host and 90% of target-host cultures, and 50:50, 90:10, respectively. Aliquots of the starting phage is then added to each co-culture in an appropriate ratio which depends largely on the phage/host minimum Multiplicity of Infection (MOI) to cause productive culture infection. This dictates the number of active viral particles per bacterium is required to cause a productive infection in a given bacterial culture. This step is illustrated by FIGS. 4, 5 and 6.

Figure 7:
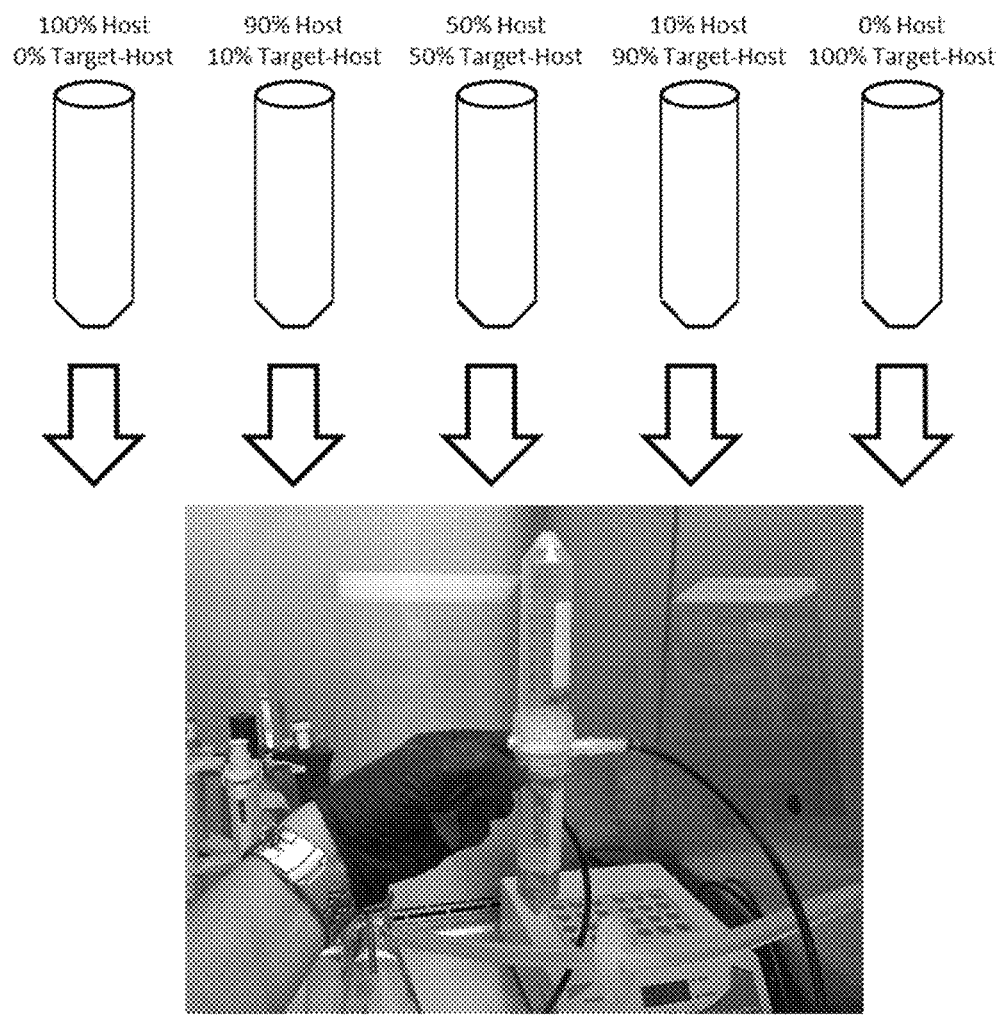
FIG. 7 illustrates an embodiment of the third step of a method according to an embodiment of the present disclosure.

Step 3:

After infection the resulting phage are separated from the bacteria in each co-culture. In an embodiment, the separation is accomplished via centrifugation at 3220×g at RT for 20 minutes and the supernatant is then passed through a 0.22 µm filter leaving purified phage particles in the filtrate. This step is illustrated by FIG. 7.

Step 4:

Purified phage from each co-culture infection are then assayed against the host and target-host organisms via double-overlay assay to check for infecting activity against each. Naïve mid-log cultures of the host and target-host bacteria are propagated and used in double-overlay assays as described in Step 1 (see FIG. 2). If plaque forming units (PFU) are formed than infective activity against the organism used in the assay is detected. This step ensures that infective activity against the original host is not lost and exposes mutant phage that have undergone the desired host-expansion event. This step is illustrated in FIG. 8.

Figure 8:
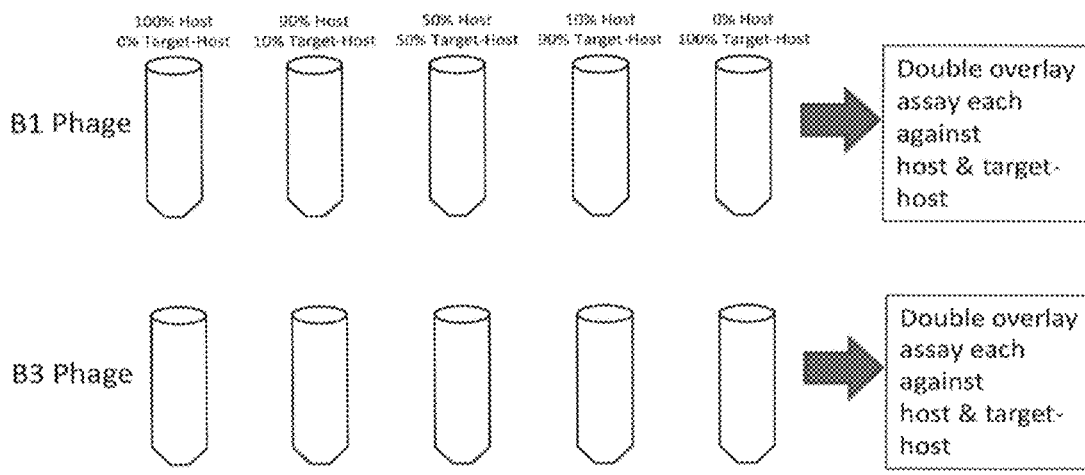
FIG. 8 illustrates an embodiment of the fourth step of a method according to an embodiment of the present disclosure.
Figure 9:
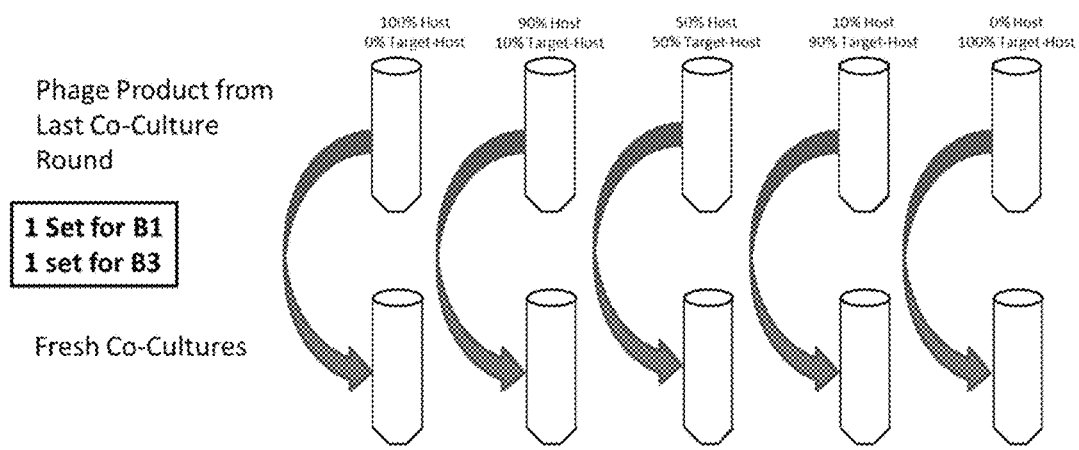
FIG. 9 illustrates an embodiment of the fifth step of a method according to an embodiment of the present disclosure.
Figure 10:
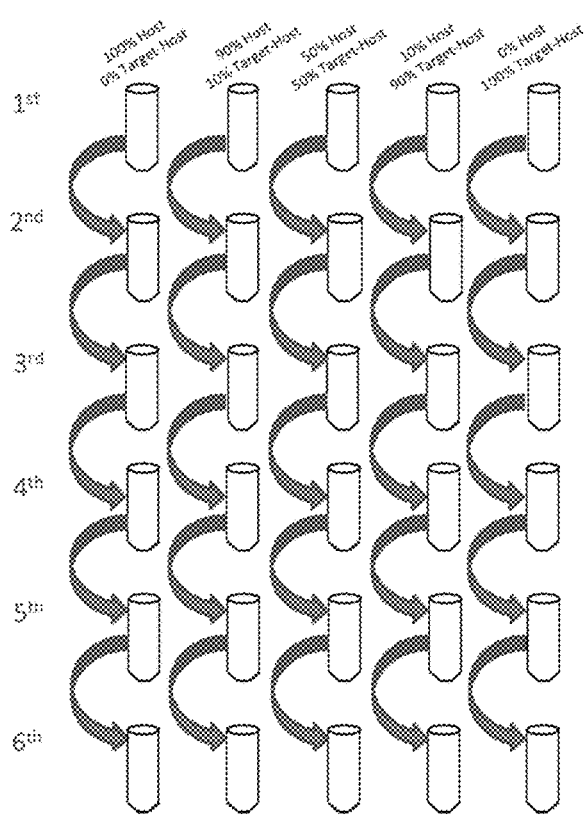
FIG. 10 illustrates an embodiment of the fifth step of a method according to an embodiment of the present disclosure.

Step 5:

The purified phage is then passaged into the corresponding co-cultures from which they were isolated as described in Step 2, isolated again as described in Step 3 (see FIG. 7), and assayed again as described in Step 4 (see FIG. 8). Passaging in this fashion is repeated until mutant phage that infects the target-host bacterial strain is detected. This step is illustrated in FIGS. 9 and 10.

Step 6:

Mutant phage that infect the target-host are isolated and expanded. This step is illustrated in FIGS. 11 and 12.

Figure 11:
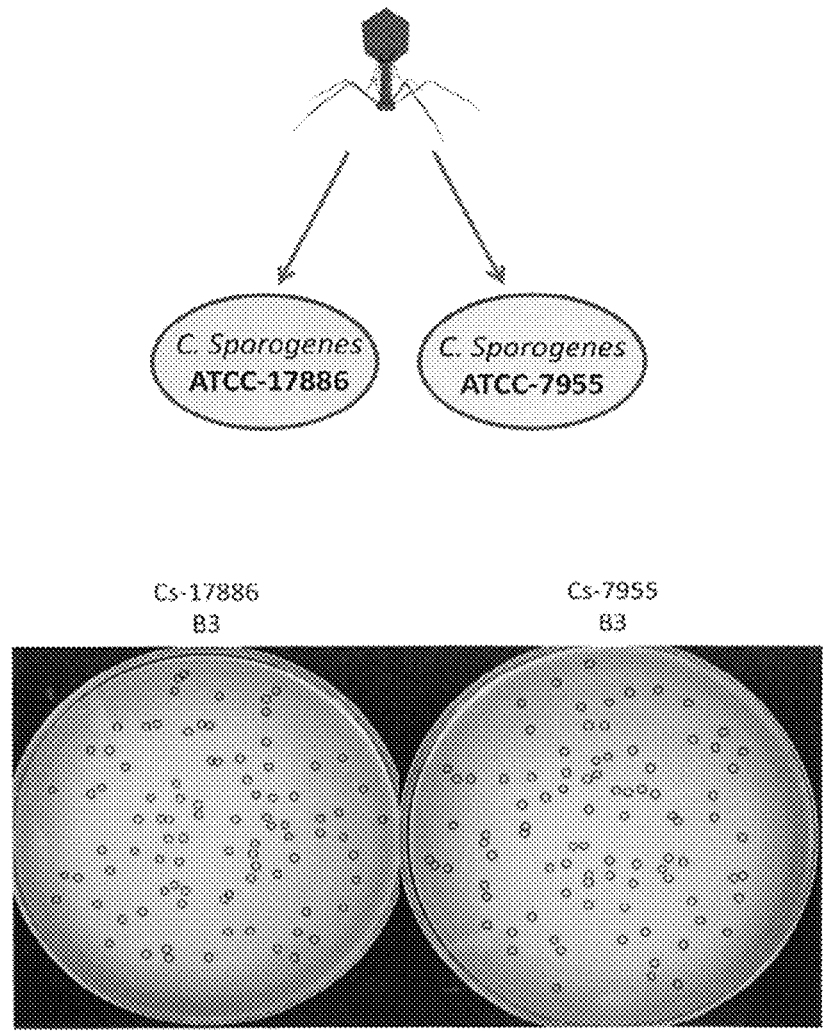
FIG. 11 illustrates an embodiment of the sixth step of a method according to an embodiment of the present disclosure.

Plaque forming units from double-overlay assays with the target-host, as shown in FIG. 11, are removed from the top agar layer of the double-overlay assay, placed into sterile buffer or broth medium, and incubated at RT for approximately 2 hours while rocking. This allows the mutant phage to escape the agar matrix and diffuse into a liquid that is not harmful to the phage. The liquid that contains the phage is then used in subsequent double-overlay assays against the target-host and isolated again in order to expand the number of mutant phage in the total phage population. When enough mutant phage is propagated to meet or exceed the required MOI for a liquid culture of target-host bacteria, aliquots of the mutant phage can then be added to a liquid culture of mid-log target-host and allowed to infect in order to expand the phage population in larger volumes than is achieved from double-overlay assays. The newly expanded phage population is then purified as described in Step 3 (see FIG. 7).

Figure 12:
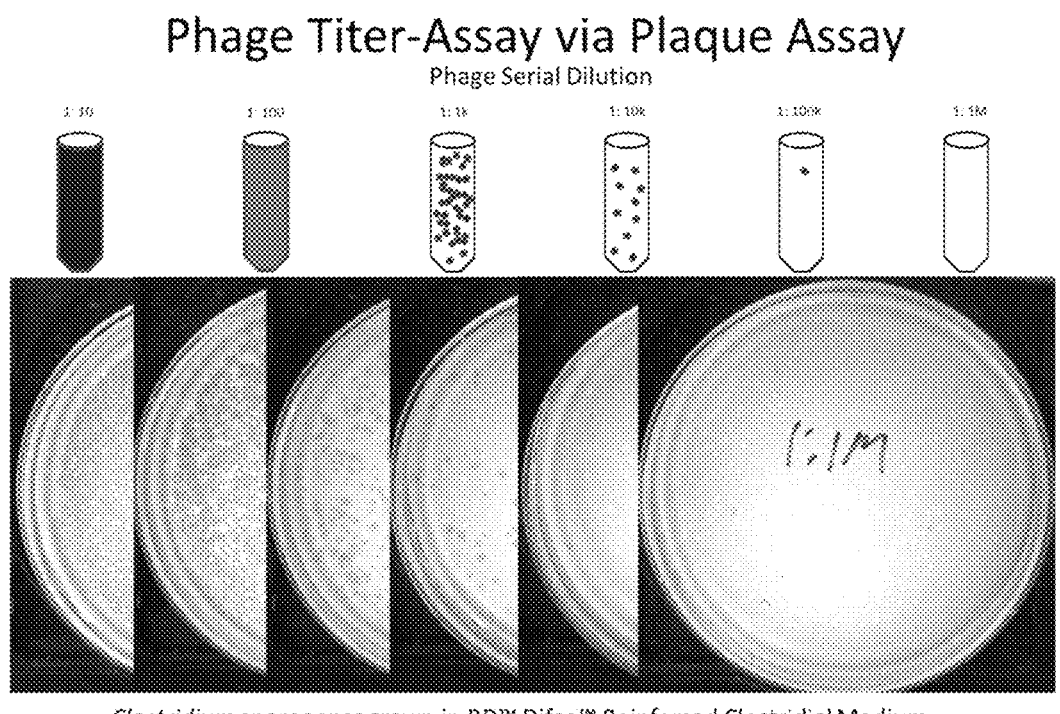
FIG. 12 illustrates an embodiment of the sixth step of a method according to an embodiment of the present disclosure.

The concentration of phage is determined by serially diluting a portion of the stock into aliquots of sterile broth medium or buffer and performing a double-overlay assay on each dilution (see FIG. 12). PFU's are counted for the dilutions that contain few enough PFU's to count and the concentration of the initial phage stock is then calculated and reported as PFU/mL of phage. This is done with both the original host and the target-host to determine the level of infecting activity the mutant phage holds for each bacterial host.

The disclosed methods present procedures that cause phage to infect a predetermined bacterial host that it otherwise would not infect. The disclosed methods further present procedures that cause phage to increase infectivity against a host that it currently is able to infect.

Example

By passaging phages in co-cultures of their natural host with increasing ratios of a target-host, the host range of two phages specific to *Clostridium sporogenes* were expanded. This adaptation was performed in both the presence and absence of a mutagen. Of twenty-eight total mutants, six were sufficiently stable to persist in target-host culture alone. Of these six, four were chosen for further analysis of their infective activity in their natural and target-hosts. Most phage populations that resulted from each passage of each co-culture infection lost infective activity against their initial host and also failed to show infecting activity in the target-host. On the other hand, there were several phage populations that demonstrated a gain of activity against one or both hosts. In some cases the gained infectivity exceeded the infective activity that was measured for the starting host at the beginning of the project. Though mutations causing host-expansion events in phages seem to occur randomly, there was a notable increase in the number of successful mutations in the presence of a mutagen as opposed to without.

Materials & Methods

Biomaterials Used: Two commercially available bacteriophages, Cs-17886-B1 and Cs-17886-B3, were obtained from the American Type Culture Collection (ATCC). Both are known to infect a specific strain of the Gram positive anaerobe *Clostridium sporogenes* (ATCC 17886) with high efficacy. The goal of these experiments was to generate and retain mutant phage strains that could productively infect a previously un-infectable "target-host" strain of *C. sporogenes* (ATCC 7955). Both *C. sporogenes* strains were also obtained from the ATCC.

Culture Medium: Both Cs-17886 and Cs-7955 were propagated in Becton, Dickinson (BD) Reinforced Clostridial Medium (BD 215192) and assayed via double-overlay assay to quantify the existing infectivity and titer against the pre-established phage-host (*C. sporogenes* ATCC 17886) as well as the infectivity and titer of potentially mutated bacteriophage against the target-host *C. sporogenes* ATCC 7955.

Anaerobic chambers: Liquid cultures and plaque assays were statically incubated overnight at 37° C. in BD Gas-Pak™ 100/150 anaerobic systems manufactured by Becton, Dickinson and Company (Franklin Lakes, N.J.

Producing host and target-host working stocks: 10 mL aliquots of BD Reinforced Clostridial broth in 15 mL glass tubes were capped with aluminum foil, steam sterilized at 121° C. for 15 min., and inoculated with 100 µL of frozen stock of either *C. sporogenes* ATCC 17886 or ATCC 7955. Frozen bacterial stocks were kept at −80° C. in 50% sterile glycerol. Inoculated cultures were statically incubated under anaerobic conditions at 37° C. for 12-15 hours. Cultures kept for more than two days at 4° C. after initial incubation were not used for assay or phage propagation purposes.

Double-overlay assay: Using a method modified from Betz and Anderson (1963), Reinforced Clostridial Medium containing 1.2% agar was poured into 4" petri dishes and allowed to cool and solidify to create a base agar layer. These plates were conditioned in an anaerobic environment at room temperature (RT) for no less than 15 hours before use. 100 µL of bacteriophage sample was then mixed with 300 µL of *C. sporogenes* culture in a 14 mL plastic test tube (Fisher 14-959-11B) using a pipette and incubated at RT for 10-20 min. After incubation the infected culture was mixed with 4 mL of BD Reinforced Clostridial Medium with 0.7% agar held at 52° C. in a thermoblock, and then poured over the solid base-agar layer in a petri dish. After allowing the top agar containing infected bacteria to cool and solidify, assay plates were then statically incubated at 37° C. under anaerobic conditions for 12-15 hrs. A Reichert Darkfield Quebec™ Colony Counter was used to count plaques.

Titer Assay: titer assays are formed by serially diluting phage samples in SM Buffer and performing a double-overlay assay on each of the diluted samples. The resulting plaques in each assay were then counted and the phage concentration of the initial sample was calculated in Plaque Forming Units (PFU) per mL.

Experiment: Upon receipt of *C. sporogenes* ATCC 17886 and *C. sporogenes* 7955, bacterial strains master and working stocks of each were propagated in BD Reinforced Clostridial Broth Medium (RCB), mixed with glycerol to 50%, flash-frozen in LN2, and stored at −80° C. Bacteriophages *C. sporogenes* 17886-B1 and *C. sporogenes* 17886-B3 were propagated separately in *C. sporogenes* ATCC 17886 cultures and the phage activity and concentrations of each was determined via double-overlay assay against the host *C. sporogenes* 17886 and target-host *C. sporogenes* 7955 (see FIG. 1). This ensured that each of the initial phage stocks was highly active against their shared host, *C. sporogenes* 17886, but not active against the target-host, *C. sporogenes* 7955.

Figure 13:
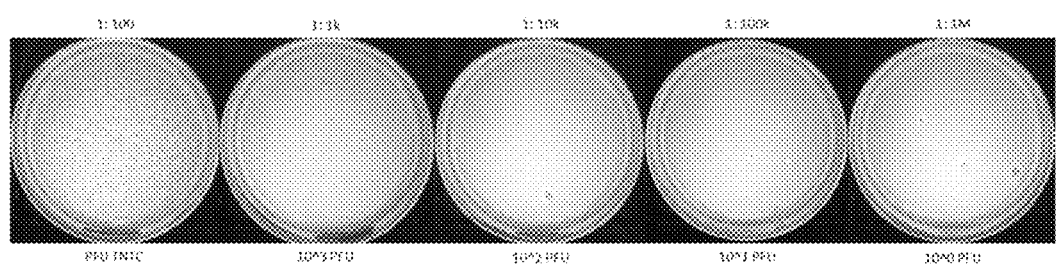
FIG. 13 shows plaque assays of null-mutagen B3 mutant bacteriophage that have been serially diluted (by log) and assayed against target-host *C. sporogenes* 7955, according to an embodiment of the disclosure.

FIG. 13 shows double-overlay assays of null-mutagen B3 mutant bacteriophage that have been serially diluted (by log) and assayed against target-host *C. sporogenes* 7955. The number of Plaque Forming Units (PFUs) decreased by order of magnitude as they have been diluted by order of magnitude. Double-overlay assays with phage isolated from co-culture infections are used to determine the presence and concentration of mutant phages that are active against the target-host.

To produce mutant phage via co-culture, the host and target-host bacterial strains were first cultured separately and then subsequently mixed in ratios of Cs-17886:Cs-7955 as 1:0, 9:1, 1:1, 1:9, and 0:1 in 10 mL cultures. Two mL of the initial B1 stock was added to each co-culture in the first set of co-cultures and B3 was added to the other. They were then allowed to incubate under static, anaerobic conditions at 37° C. for 12-15 hours. The resulting progeny phage from each co-culture were purified by centrifugation (Eppendorf 5810) at 3220×g for 20 min. and the supernatant filtered through a 0.22 µm polyethersulfone (PES) filter (Millipore Steriflip™). Fresh sets of mid-log co-cultures containing bacteria naïve to the phage, were then infected with the newly purified bacteriophage progeny. Bacteriophage cultivated in each co-culture ratio was passaged in this manner six times under the same corresponding conditions. The phage concentration of those infecting the host and target-host, were determined by titer assay that consist of serially diluting the phage stock and performing a double-overlay assay on each of the dilutions (see FIG. 12). Titer assays were used to determine the resulting infectivity against the target-host as well as the original host.

Table 1 (FIG. 22) shows the results of plaque assays using 100% target-host used to expose mutants contained in a sample taken from the product of each null mutagen phage passage. Assays containing plaques, and thus mutant phage, are highlighted in bold. Results from each co-culture infection using B1 (passages 1-6) are listed in the top six rows and that of B3 are listed in the bottom six rows.

Mutant phages infecting the target-host, *C. sporogenes* ATCC 7955 were isolated from agar plaques by diffusion into 100 μL of sterile SM buffer. These samples were then centrifuged at 3220×g for 10-20 min. to separate the agar from the phage. The resulting phage-rich supernatant was then used in another double-overlay assay containing only target-host for the purpose of increasing the phage population from the plaque(s). By propagating the mutant phage population the mutation was then "fixed" in the entire phage population that carries the desired mutation instead of only a small number of viral particles. Though many plaque isolates failed to propagate, the mutations which were successfully fixed were further propagated using the same method against only the target-host until enough active phages existed that the genomic DNA could be extracted, purified and sequenced.

To increase the frequency of mutations, Mitomycin C was added to cultures in some experiments. Mitomycin C causes pyrimidine dimers in DNA and is often used to mimic the genomic mutations associated with exposure to UV-C radiation (Levine 1960). Mitomycin C was added to each co-culture upon phage passaging to a final concentration of 1 μg/mL (Levine 1960; Kiritani, et. al 1973).

Results

Stocks of Cs-17886-B1 and Cs-17886-B3 phage were each propagated using *C. sporogenes* ATCC 17886 as the host in liquid cultures. The resulting phage stocks were purified and used in phage genomic DNA isolations and in host-expansion experiments. Initial B1 and B3 phage stocks were verified to be infectious against *C. sporogenes* ATCC 17886 but not to *C. sporogenes* ATCC 7955 using double-overlay assays. The concentrations of the initial B1 and B3 phages were determined to be 3.4×10ˆ7 PFU/mL and 1.9×10ˆ8 PFU/mL, respectively by titer assay.

Each phage stock was individually incubated in *C. sporogenes* co-cultures as previously described, harvested, and used to infect naïve, bacterial co-cultures for a total of six passages. After each passage, the phage products were passed through a 0.22 μm filter and stored at 4° C. Titer assays on each phage product using the target-host only were performed to expose phage mutants (see Table 1).

Plaques that appeared when only the target-host strain was used revealed mutant phages that had expanded their host range but the reproducibility in some of the mutants that were harvested was limited. A slight bias in all mutants toward co-cultures containing higher concentrations of natural-host was observed however no bias was seen in the number of passages required to gain or lose mutant phage (see Table 1). This random mutation pattern lends itself to a low predictability of the appearance of Single Productive Mutations (SPMs). A more pronounced bias of B3 SPM's than that of B1 toward co-culture infections with higher concentrations of natural-host was seen (see Tables 1 & 2).

Table 2 (FIG. 23) shows the results of plaque assays using 100% target-host to screen for mutants contained in a sample taken from the product of each phage passage into cultures containing 1 μg/mL Mitomycin C. Results from each co-culture infection using B1 (passages 1-6) are listed in the top six rows and that of B3 are listed in the bottom six rows. As is evident, the cultures containing plaques must contain mutant phage.

Adding Mitomycin C (MC) to a final concentration of 1 μg/mL along with the phage populations being passaged caused SPM's of B1 and B3 to occur more frequently and to follow a pronounced bias toward co-cultures with higher concentrations of host strain (see Table 2). Additionally, more total plaques were seen in each co-culture infection screening. This suggests a correlation between the presence of Mitomycin C and the frequency of phage mutation producing SPMs (see Table 2).

As host-expanded mutant phages were discovered, they were separated from the agar-based plaque and allowed to propagate further in 100% target-host culture. Plaques were removed by forcing the tip of a sterile glass Pasteur pipette through the top agar layer and expelling the resulting plug into a small conical vial containing SM buffer. Phages were then allowed time to escape the agar matrix and diffuse into the buffer. After incubating at room temperature for 2-4 hours, the buffer was removed and used in a subsequent plaque assay so to propagate the mutant phage and further build the overall population. This was repeated until the mutant phage population had grown large enough to perform a successful liquid infection in a pure target-host liquid culture. Liquid infections were then centrifuged, the supernatant passed through a 0.22 μm filter, and titer assayed to determine the mutant phage concentration. These routine titer assays not only confirmed their continued phage activity against the target-host but also provided a means to determine the mutant phage concentration within each mutant phage expansion.

A total of 28 mutant phage variants were detected, six of which were successfully "fixed" as mutants and were able to propagate in 100% target-host culture (Table 3, FIG. 24). Of the six fixed mutants, four were chosen for further analysis. The four phage mutants that were chosen represent both B1 and B3 phage mutants as well as each of the co-culture environments where MC was added and where it was not (see Tables 3 & 4, FIGS. 24 & 25).

Table 3 shows phage mutants discovered from plaque assays (100% target-host) performed on the filtered product from each co-culture passage. Left: mutants discovered from co-cultures containing no MC. Right: mutant phage discovered from co-cultures containing MC. B1-MC yielded 3 mutant phage strains where B1+MC yielded 5. B3-MC yielded 7 mutant phage where B3+MC yielded 13.

Table 4 (FIG. 25) shows the amount of total RNA, dsDNA, and ssDNA that was isolated from the initial B1 and B3 phage strains after pretreating each purified phage sample with various endonucleases and exonucleases to remove free nucleic acids that are not related to the genome of the phages. RNAse and DNAse treatments digested free RNA and DNA respectively prior to the isolations of the phage genomes. It is shown that RNA was present in each purified phage sample before they were treated with RNAse but absent after. This indicates that upon the isolation of each phage genome, no RNA was present among the purified phage samples. No RNA was detected after each genome was isolated either indicating that neither phage genome is comprised of RNA. ssDNA and dsDNA were also measured before the phage genomes were isolated and both were found to be present. Readings for each after a DNAse treatment indicate that, with the exception of the ssDNA in the B1 sample, the free DNA in each sample were significantly reduced before the genomes were isolated. Though the concentrations of dsDNA and ssDNA were comparable between B1 and B3 after the treated genome isolations, there was double the amount of ssDNA in the B3 sample as in the B1 in the genome isolations that did not include a DNAse pretreatment. The B1 genome has already been previously determined to be of dsDNA and its sequence has been published. Armed with this information the B1 genome was analyzed alongside the B3 genome as a benchmark for comparison.

The two selected mutants that were derived from −MC conditions include B1 from the third passage of 100% host culture and B3 from the fourth passage of the 90% host: 10% target-host co-culture infection. The two selected mutants selected from +MC conditions include B1 from the sixth passage of 50% host: 50% target-host co-culture, and B3 from the fifth passage of 90% host: 10% target-host co-culture.

Concentrations of phage populations from each passage was determined through titer assays of 100% host-culture infections. As a result, growth fluctuations with similar trends were seen across phage populations and were used to determine phage infectivity gain or loss to the original-host (see FIGS. 14A-14D, 15A-15D, 16A-16D, 17A-17D, and 18A-18D). Titer assays, using 100% host, were performed using the product of each −MC and +MC passage for B1 and B3 (see FIGS. 14A-14D). This growth cycle was used as a benchmark to compare the growth cycles observed in the other phage populations. It should be noted that where the −MC and +MC B1 growth cycles are similar, those of B3 are nearly completely out-of-phase.

Figure 14A:
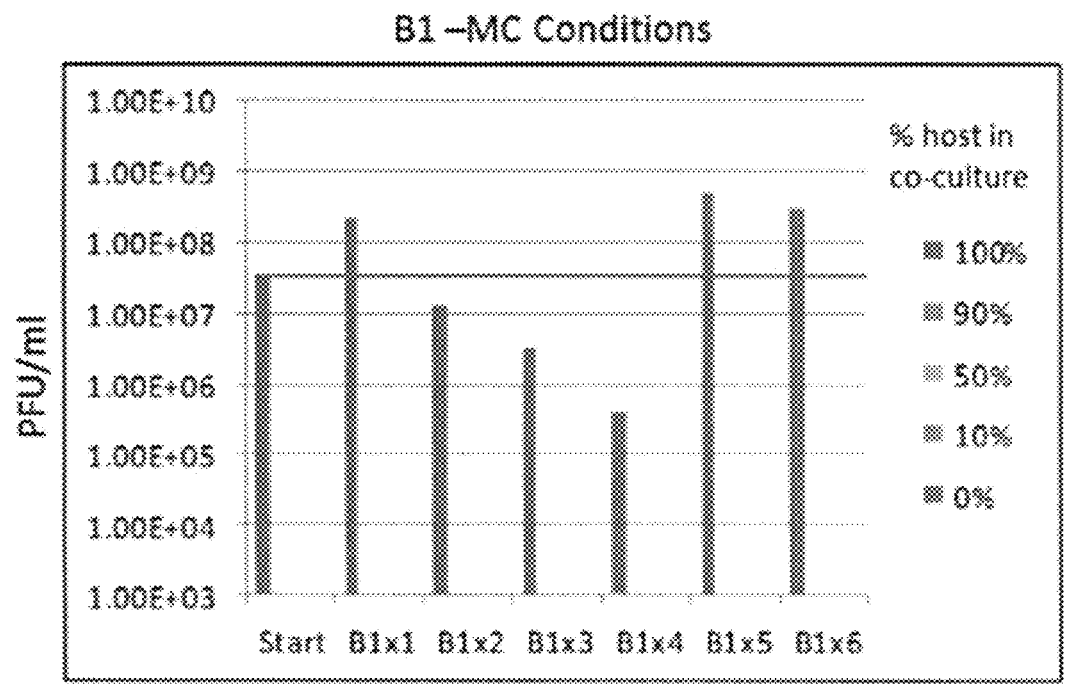
FIG. 14A shows B1φ that was passaged through host cultures containing no mutagen with the starting titer of 3.4E+7 PFU/mL, depicting its natural infectivity cycle when passaged into 100% natural host six times, according to an embodiment of the disclosure.
Figure 14B:
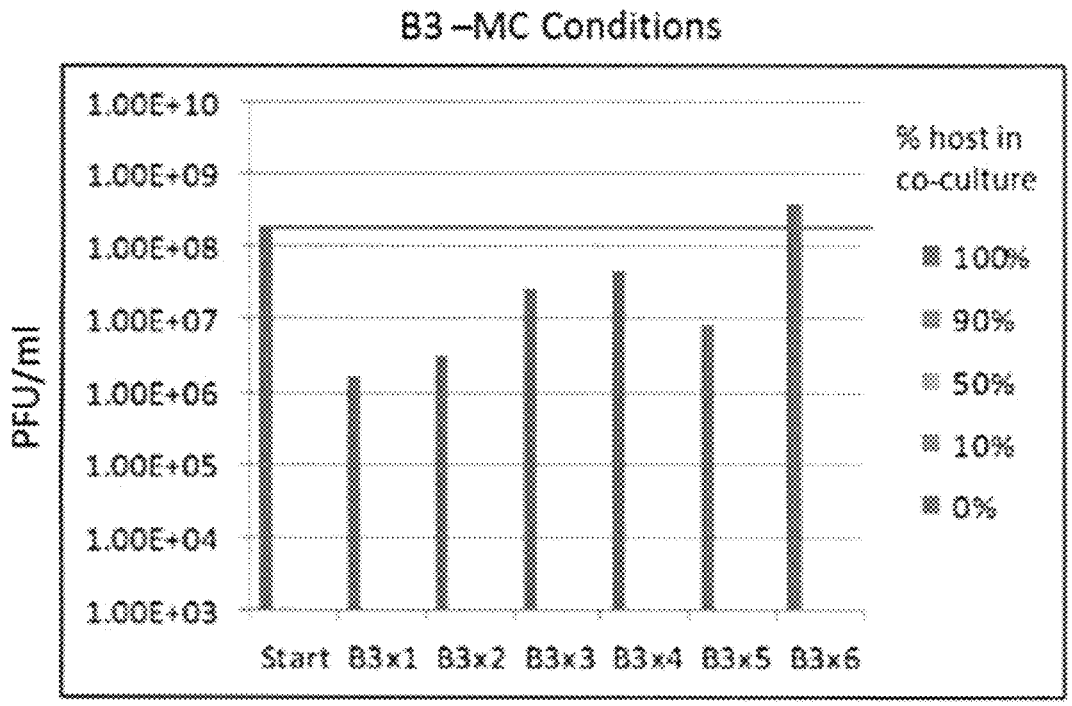
FIG. 14B shows B3φ that was passaged through host cultures containing no mutagen with the starting titer of 1.9E+8 PFU/mL, depicting its natural infectivity cycle when passaged into 100% natural host six times, according to an embodiment of the disclosure.
Figure 14C:
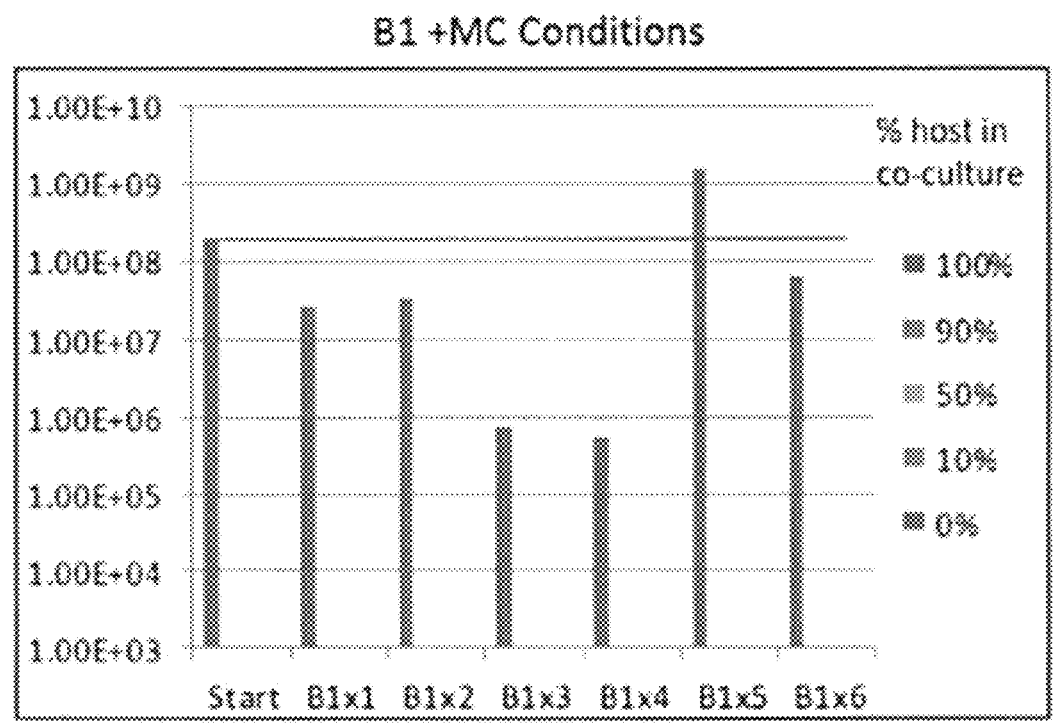
FIG. 14C shows B1φ that was passaged through host cultures containing a mutagen (1 µg/mL Mitomycin C) with the starting titer of 3.4E+7 PFU/mL, depicting its natural infectivity cycle under mutagenic stress when passaged into 100% natural host six times, according to an embodiment of the disclosure.
Figure 14D:
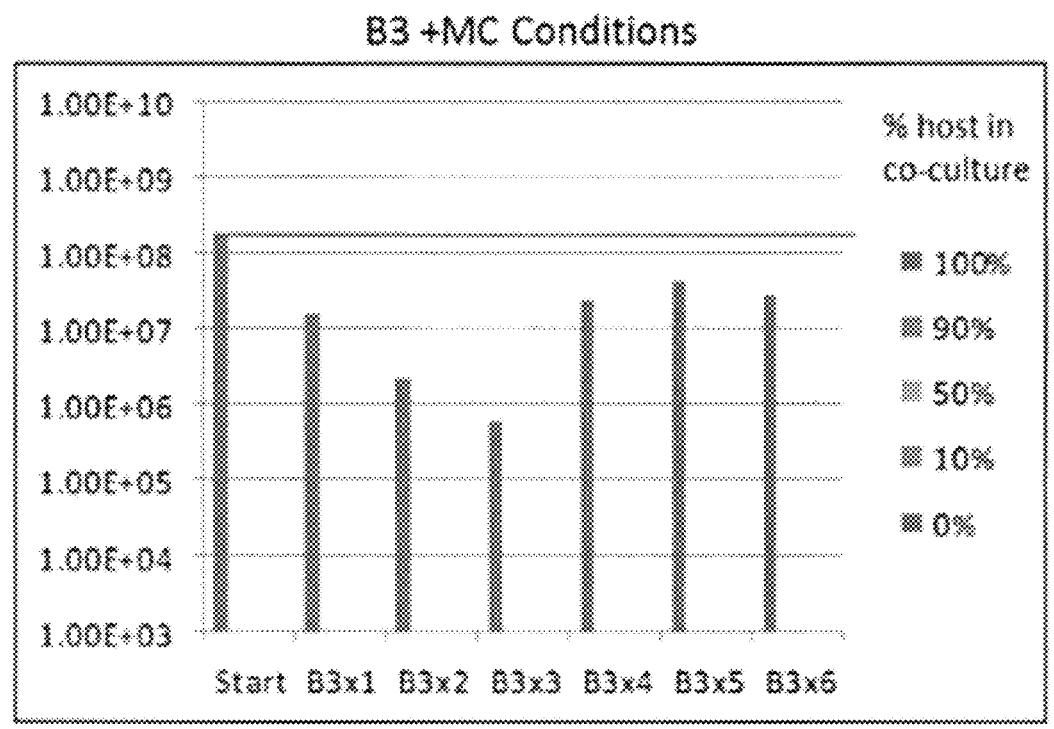
FIG. 14D shows B1φ that was passaged through host cultures containing a mutagen (1 µg/mL Mitomycin C) with the starting titer of 1.8E+8 PFU/mL, depicting its natural infectivity cycle under mutagenic stress when passaged into 100% natural host six times, according to an embodiment of the disclosure.

FIGS. 14A-14D show the resulting phage titers from each passage against original host for B1 and B3 under mutagenic and null-mutagenic conditions and depict the natural infectivity cycle of each phage when passaged into 100% natural host. FIGS. 14A and 14B show the resulting concentrations of B1ϕ and B3ϕ passaged under no artificial mutagenic stress. FIGS. 14C and 14D show the resulting concentrations of B1ϕ and B3ϕ passaged in the presence of 1 μg/mL Mitomycin C.

Figure 15A:
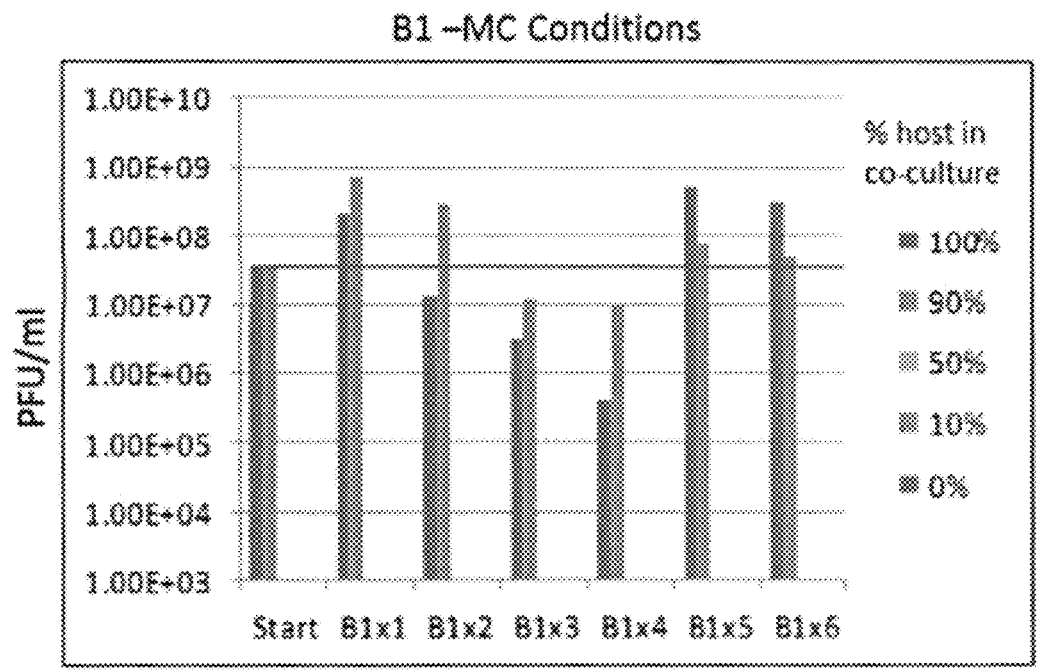
FIG. 15A shows B1φ passaged through co-cultures containing no mutagen with the starting titer 3.4E+7 PFU/mL, depicting a comparison in titer yield from passaging B1φ into co-cultures that contained 90% host and 10% target-host with the natural infectivity cycle across pure host cultures and how this trend follows the natural infectivity cycle of B1φ but to a greater extent, according to an embodiment of the disclosure.
Figure 15B:
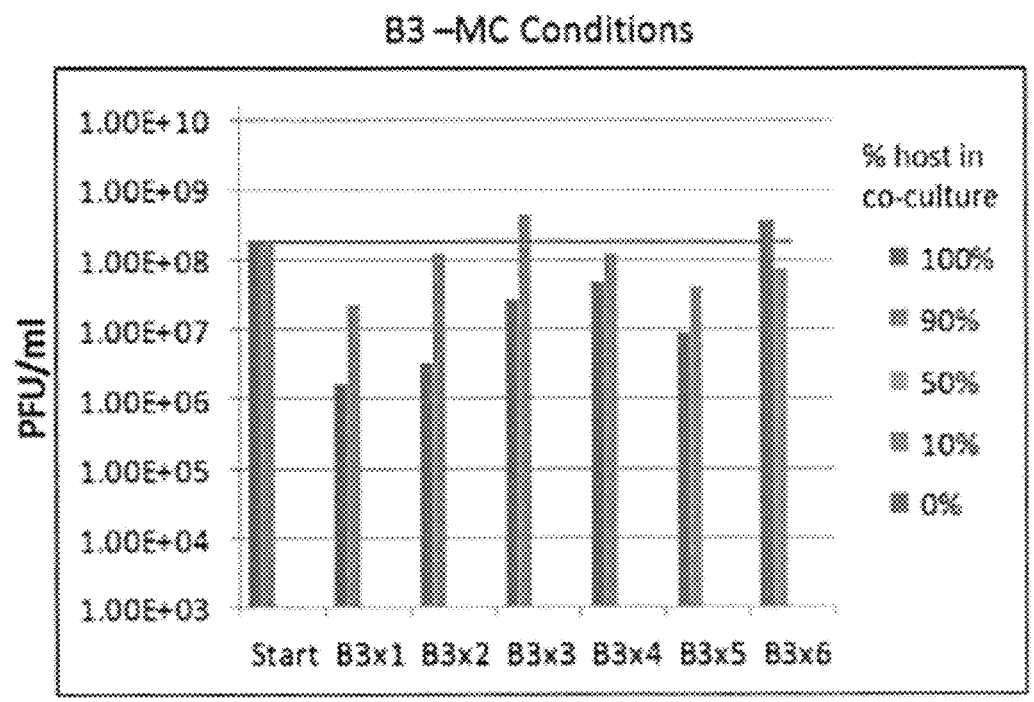
FIG. 15B shows B3φ passaged through co-cultures containing no mutagen with the starting titer 1.9E+8 PFU/mL, depicting a comparison in titer yield from passaging B3φ into co-cultures that contained 90% host and 10% target-host with the natural infectivity cycle across pure host cultures and how this trend follows the natural infectivity cycle of B3φ but to a greater extent, according to an embodiment of the disclosure.
Figure 15C:
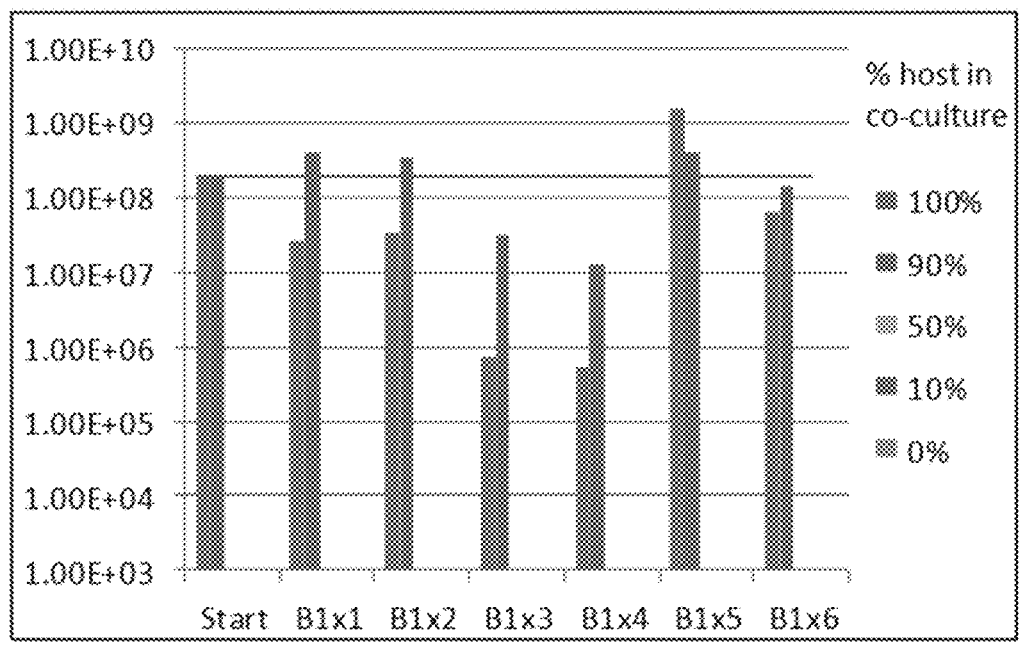
FIG. 15C shows B1φ passaged through co-cultures containing a mutagen (1 µg/mL Mitomycin C) with the starting titer 3.4E+7 PFU/mL, depicting a comparison in titer yield from passaging B1φ into co-cultures that contained the same mutagen, 90% host and 10% target-host with the natural infectivity cycle under mutagenic stress across pure host cultures and how this trend follows the natural infectivity cycle of B1φ but to a greater extent, according to an embodiment of the disclosure.
Figure 15D:
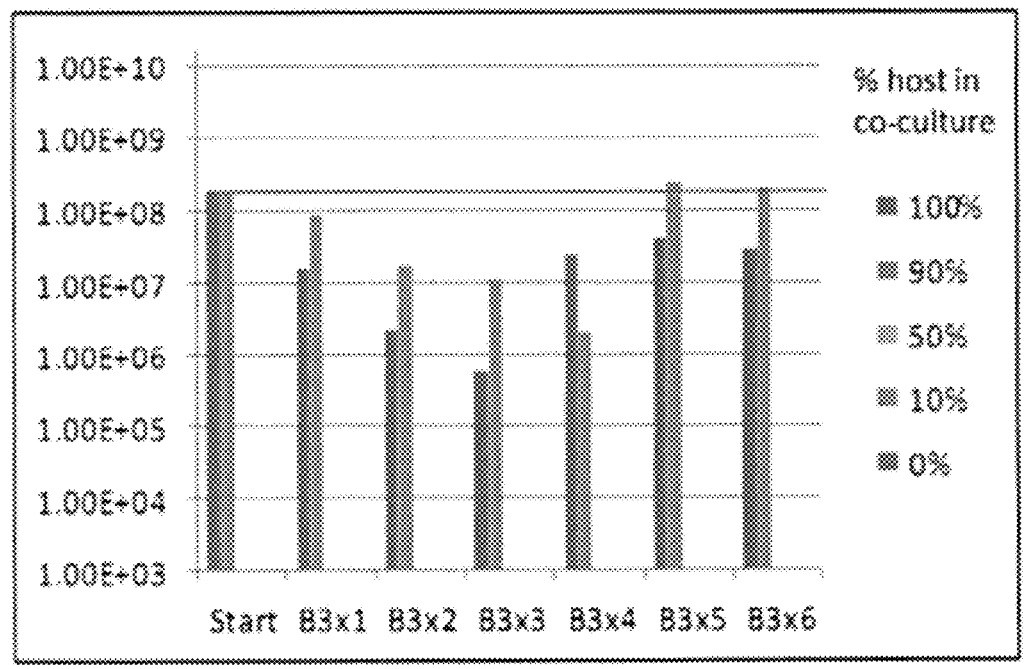
FIG. 15D shows B3φ passaged through co-cultures containing a mutagen (1 µg/mL Mitomycin C) with the starting titer 1.9E+8 PFU/mL, depicting a comparison in titer yield from passaging B3φ into co-cultures that contained the same mutagen, 90% host and 10% target-host with the natural infectivity cycle under mutagenic stress across pure host cultures and how this trend follows the natural infectivity cycle of B3φ but to a greater extent, according to an embodiment of the disclosure.

FIGS. 15A-15D compares the resulting phage titers from each passage through cultures containing 100% host to those containing 90% host and 10% target-host, assayed against original host. Titers resulting from the co-cultures follow the natural infectivity cycle found in passaging across cultures containing host only. FIGS. 15A and 15B compare the resulting concentrations of each phage type under null mutagen conditions where FIGS. 15C and 15D compare them under mutagenic stress.

Figure 16A:
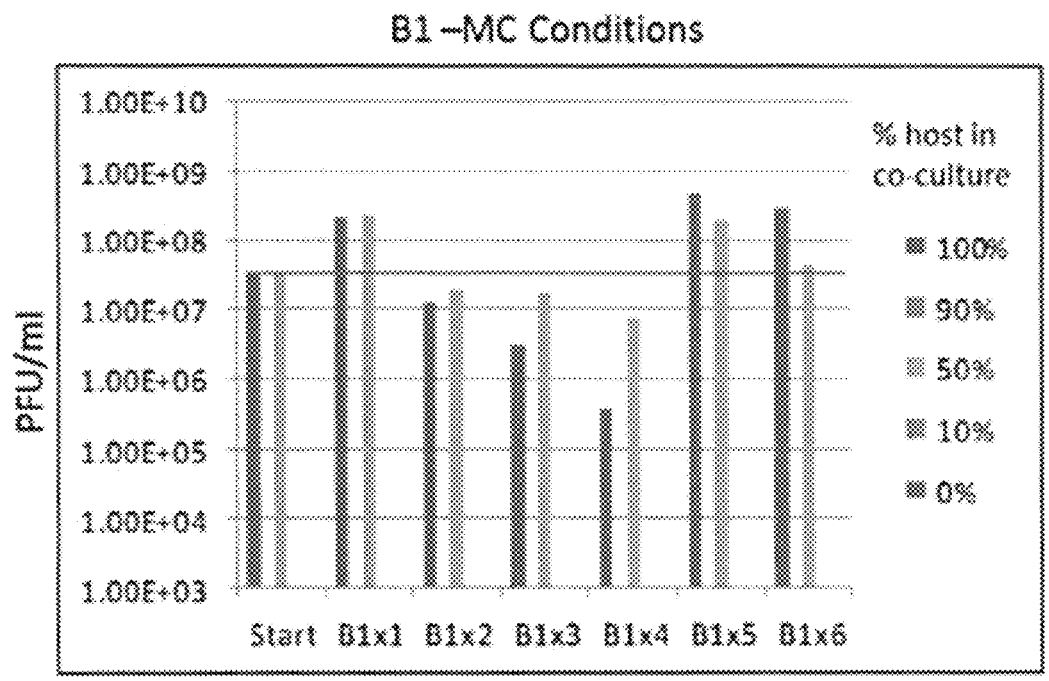
FIG. 16A shows B1φ passaged through co-cultures containing no mutagen with the starting titer 3.4E+7 PFU/mL, depicting a comparison in titer yield from passaging B1φ into co-cultures that contained no mutagen, 50% host and 50% target-host with the natural infectivity cycle across pure host cultures and how this trend follows the natural infectivity cycle of B1φ but to a greater extent, according to an embodiment of the disclosure.
Figure 16B:
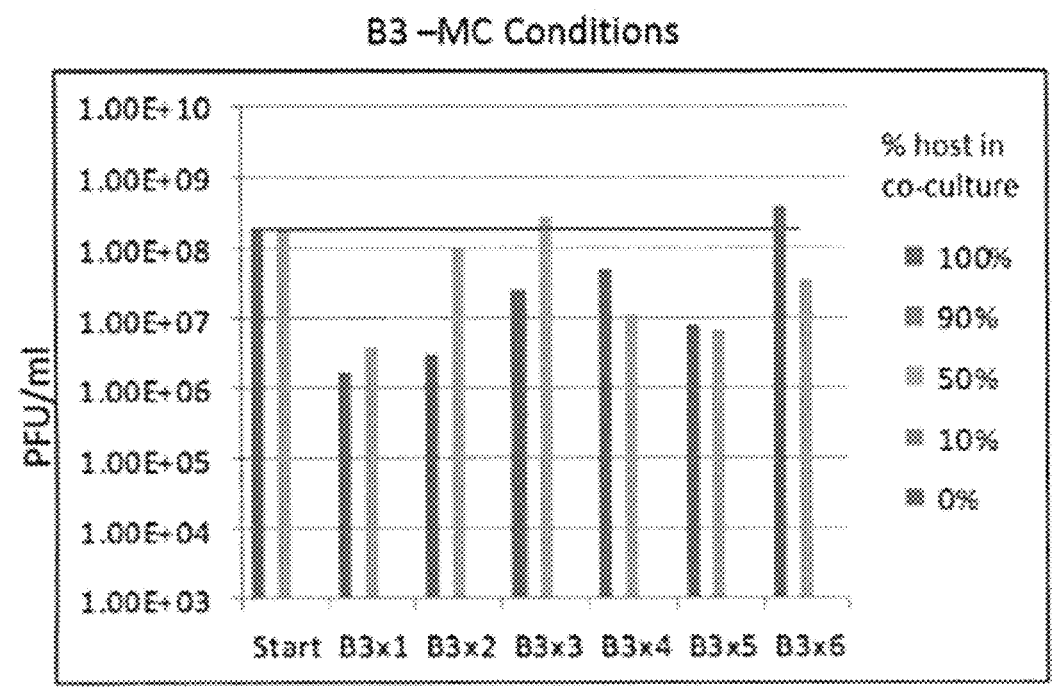
FIG. 16B shows B3φ passaged through co-cultures containing no mutagen with the starting titer 1.9E+8 PFU/mL, depicting a comparison in titer yield from passaging B3φ into co-cultures that contained no mutagen, 50% host and 50% target-host with the natural infectivity cycle across pure host cultures and how this trend follows the natural infectivity cycle of B3φ but to a greater extent, according to an embodiment of the disclosure.
Figure 16C:
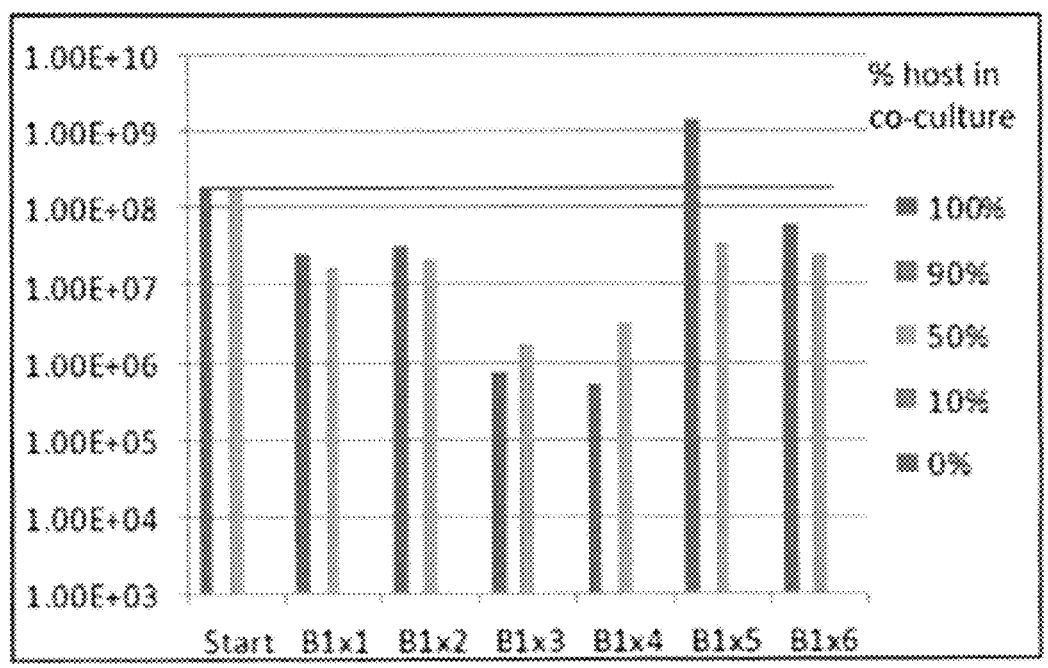
FIG. 16C shows B1φ passaged through co-cultures containing a mutagen (1 µg/mL Mitomycin C) with the starting titer 3.4E+7 PFU/mL, depicting a comparison in titer yield from passaging B1φ into co-cultures that contained the same mutagen, 50% host and 50% target-host with natural infectivity cycle under mutagenic stress across pure host cultures and how this trend follows the natural infectivity cycle of B1φ but to a greater extent, according to an embodiment of the disclosure.
Figure 16D:
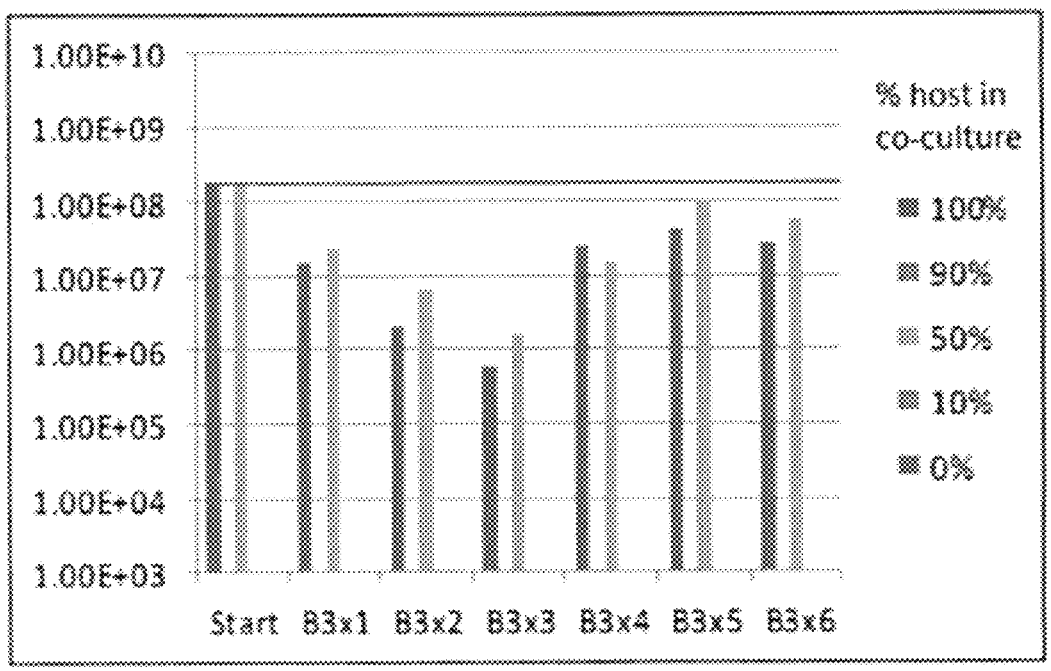
FIG. 16D shows B3φ passaged through co-cultures containing a mutagen (1 µg/mL Mitomycin C) with the starting titer 1.9E+8 PFU/mL, depicting a comparison in titer yield from passaging B3φ into co-cultures that contained the same mutagen, 50% host and 50% target-host with the natural infectivity cycle under mutagenic stress across pure host cultures and how this trend follows the natural infectivity cycle of B3φ but to a greater extent, according to an embodiment of the disclosure

FIGS. 16A-16D compares the resulting phage titers from each passage through cultures containing 100% host to those containing 50% host and 50% target-host, assayed against original host. Titers resulting from the co-cultures follow the natural infectivity cycle found in passaging across cultures containing host only. FIGS. 16A and 16B compare the resulting concentrations of each phage type under null mutagen conditions where FIGS. 16C and 16D compare them under mutagenic stress.

Figure 17A:
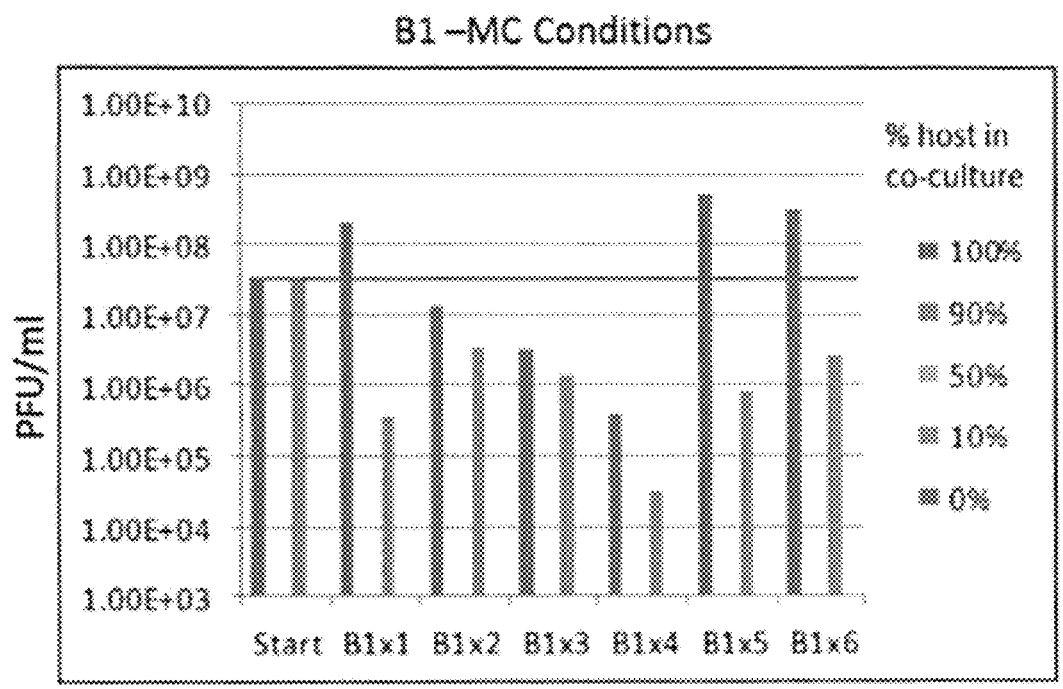
FIG. 17A shows B1φ passaged through co-cultures containing no mutagen with the starting titer 3.4E+7 PFU/mL, depicting a comparison in titer yield from passaging B1φ into co-cultures that contained no mutagen, 10% host and 90% target-host with the natural infectivity cycle across pure host cultures and how this trend follows the natural infectivity cycle of B1φ, according to an embodiment of the disclosure.
Figure 17B:
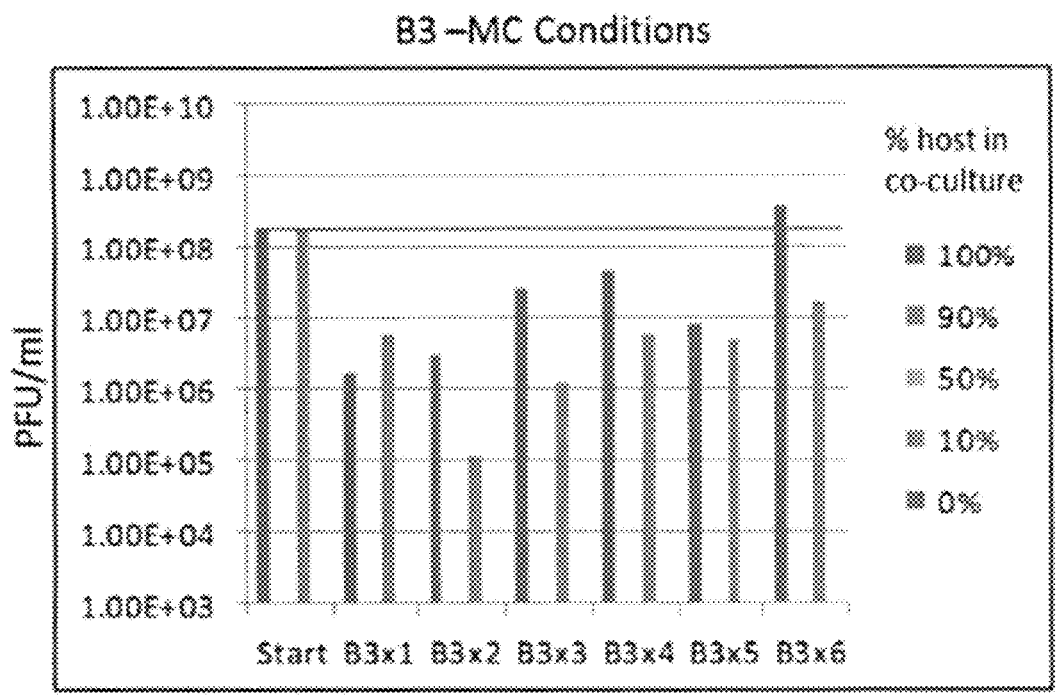
FIG. 17B shows B3φ passaged through co-cultures containing no mutagen with the starting titer 1.9E+8 PFU/mL, depicting a comparison in titer yield from passaging B3φ into co-cultures that contained no mutagen, 10% host and 90% target-host with the natural infectivity cycle across pure host cultures and how this trend follows the natural infectivity cycle of B3φ but to a lesser extent, according to an embodiment of the disclosure.
Figure 17C:
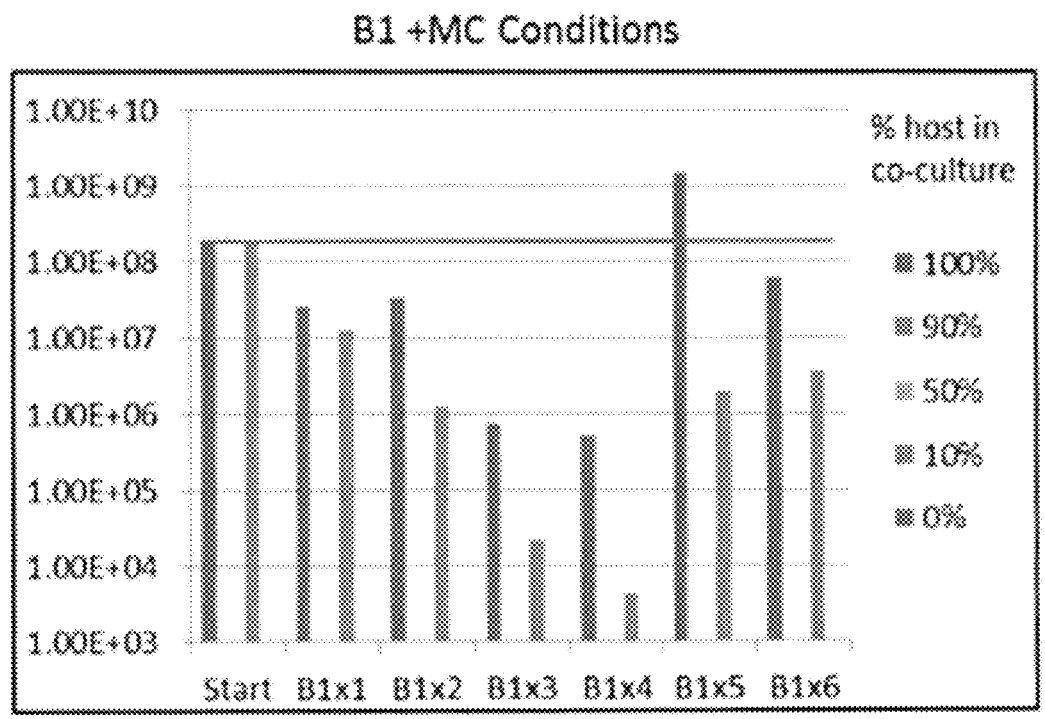
FIG. 17C shows B1φ passaged through co-cultures containing a mutagen (1 µg/mL Mitomycin C) with the starting titer 3.4E+7 PFU/mL, depicting a comparison in titer yield from passaging B1φ into co-cultures that contained the same mutagen, 10% host and 90% target-host with natural infectivity cycle under mutagenic stress across pure host cultures and how phage populations show simple dilution loss between passages except for the B1φ under Mutagen-Added conditions where a population rebound is shown, according to an embodiment of the disclosure.
Figure 17D:
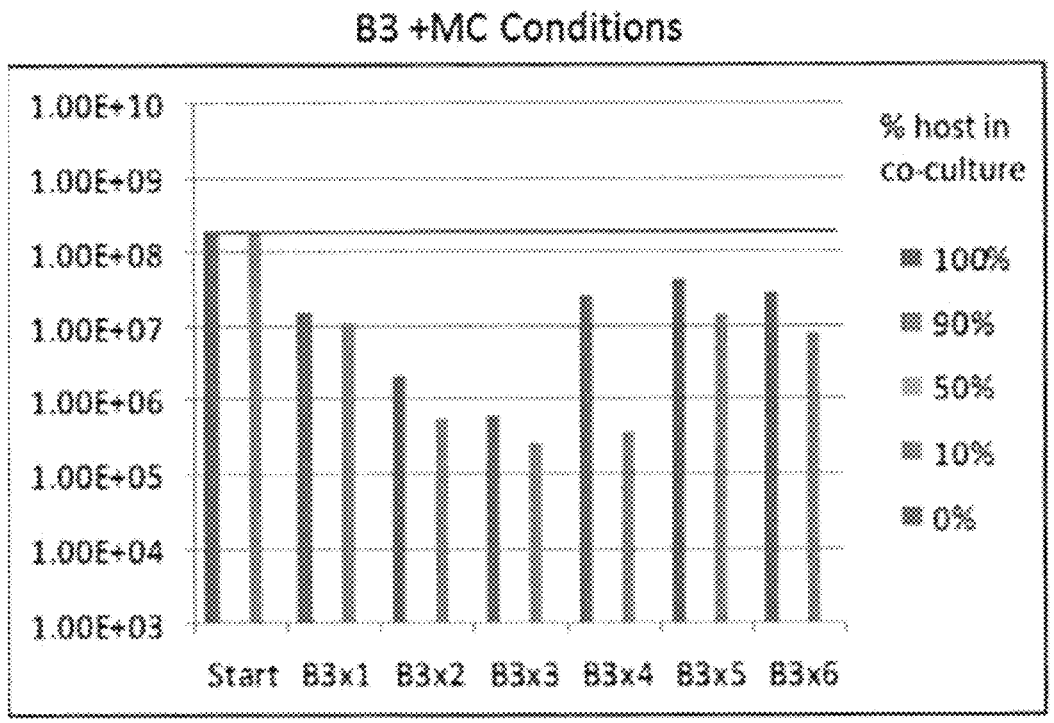
FIG. 17D shows B3φ passaged through co-cultures containing a mutagen (1 µg/mL Mitomycin C) with the starting titer 1.9E+8 PFU/mL, depicting a comparison in titer yield from passaging B3φ into co-cultures that contained the same mutagen, 10% host and 90% target-host with the natural infectivity cycle under mutagenic stress across pure host cultures and how, phage populations show simple dilution loss between passages except for the B3φ under Mutagen-Added conditions where a population rebound is shown, according to an embodiment of the disclosure.

FIGS. 17A-17D compares the resulting phage titers from each passage through cultures containing 100% host to those containing 10% host and 90% target-host, assayed against original host. Titers resulting from the co-cultures follow the natural infectivity cycle found in passaging across cultures containing host only. FIGS. 17A and 17B compare the resulting concentrations of each phage type under null mutagen conditions where FIGS. 17C and 17D compare them under mutagenic stress.

Figure 18A:
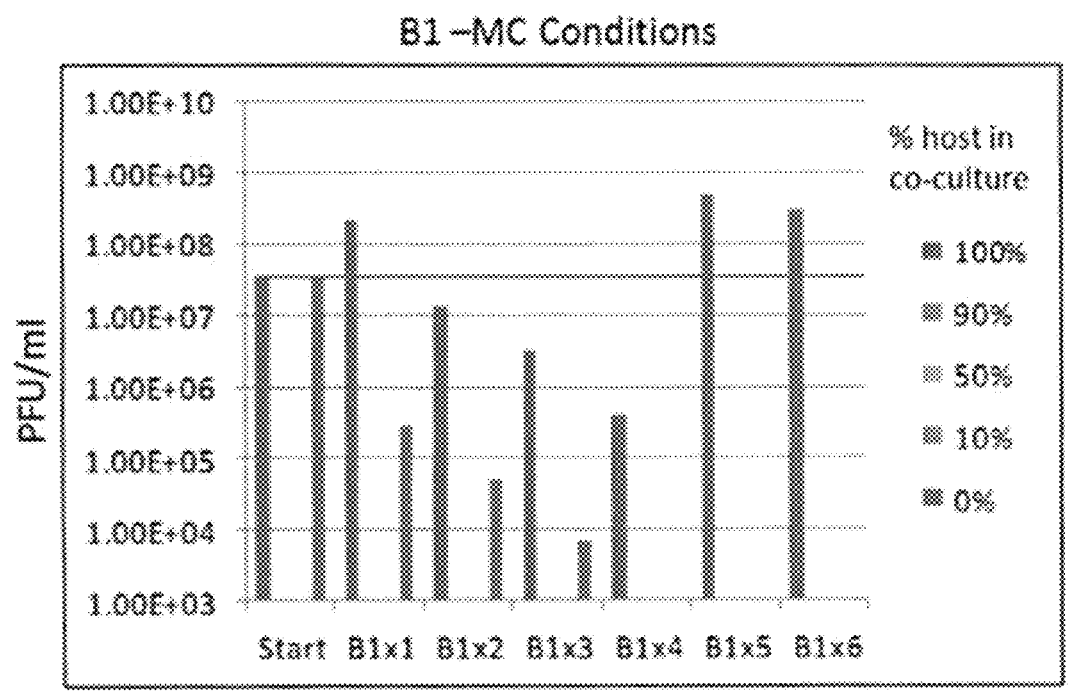
FIG. 18A shows B1φ passaged through cultures containing no mutagen with the starting titer 3.4E+7 PFU/mL, depicting a comparison in titer yield from passaging B1φ into cultures that contained no mutagen and 100% target-host with the natural infectivity cycle across pure host cultures and how phage populations show simple dilution loss between passages with no population rebound when cultivated with only the target-host, according to an embodiment of the disclosure.
Figure 18B:
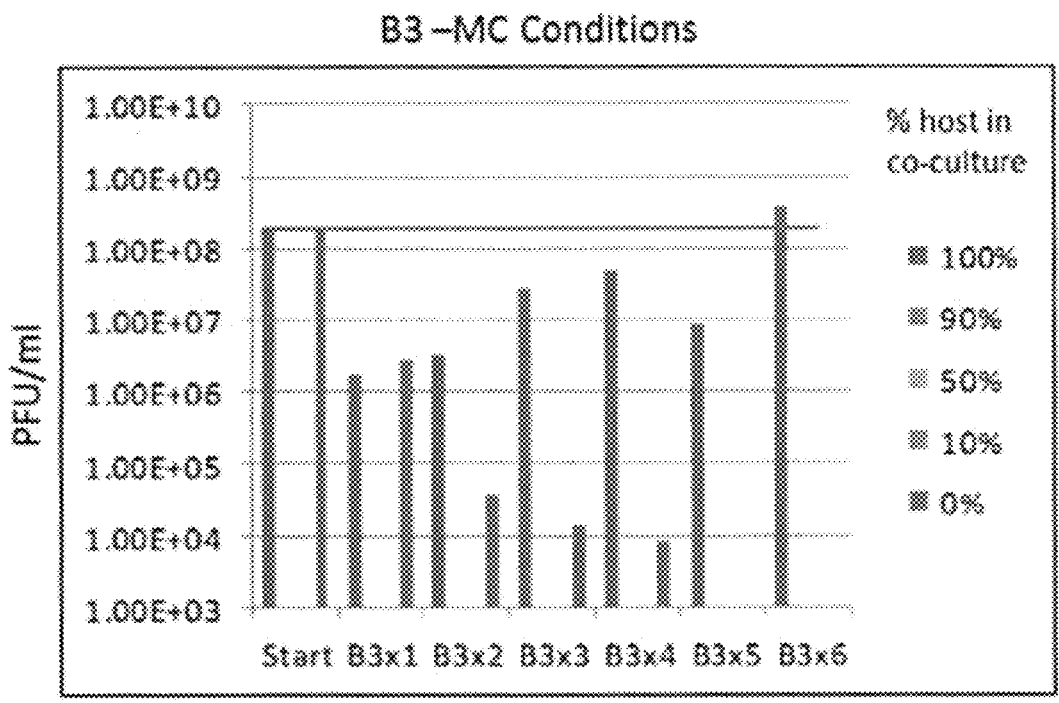
FIG. 18B shows B3φ passaged through co-cultures containing no mutagen with the starting titer 1.9E+8 PFU/mL, depicting a comparison in titer yield from passaging B3φ into cultures that contained no mutagen and 100% target-host with the natural infectivity cycle across pure host cultures and how phage populations show simple dilution loss between passages with no population rebound when cultivated with only target-host, according to an embodiment of the disclosure.
Figure 18C:
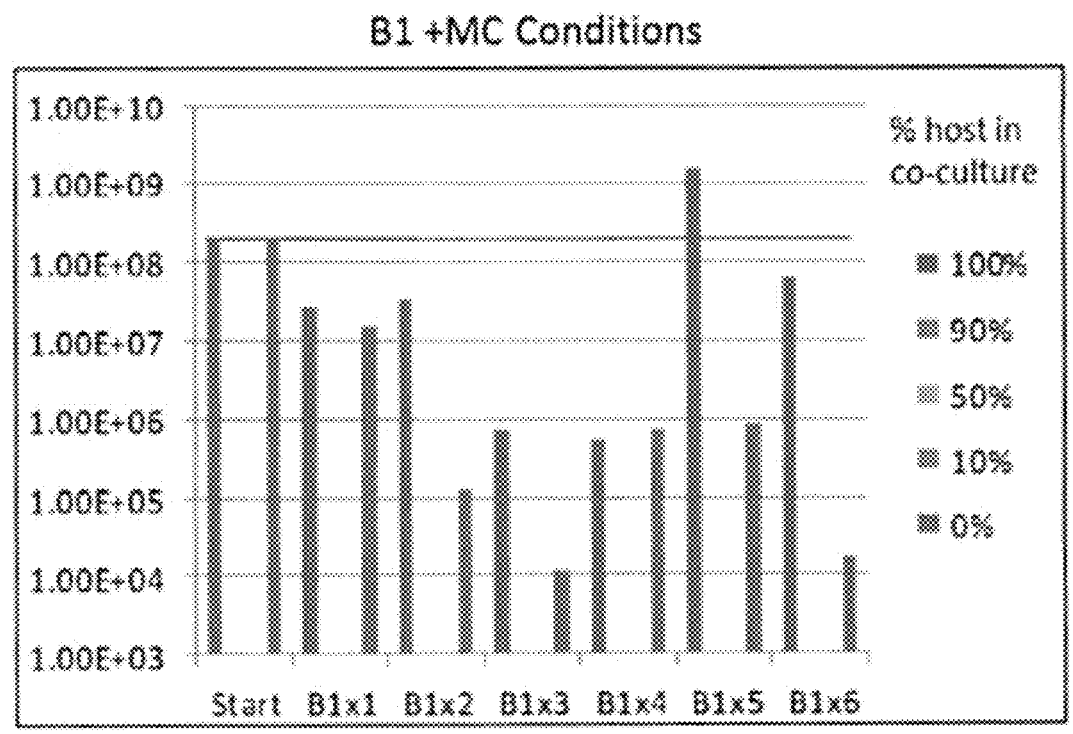
FIG. 18C shows B1ϕ passed through co-cultures containing a mutagen (1 μg/mL Mitomycin C) with the starting titer 3.4E+7 PFU/mL, depicting a comparison in titer yield from passaging B1ϕ into co-cultures that contained the same mutagen and 100% target-host with natural infectivity cycle under mutagenic stress across pure host cultures and how phage populations show simple dilution loss between passages but then rebound and decline again, according to an embodiment of the disclosure.
Figure 18D:
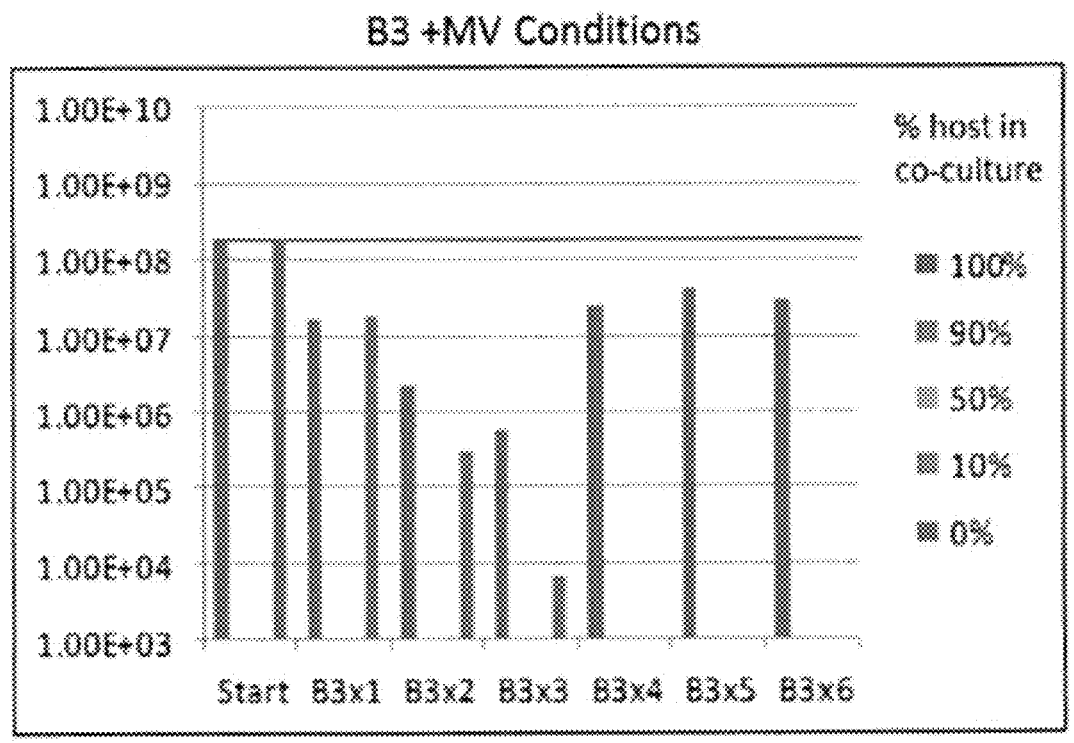
FIG. 18D shows B3ϕ passed through co-cultures containing a mutagen (1 μg/mL Mitomycin C) with the starting titer 1.9E+8 PFU/mL, depicting a comparison in titer yield from passaging B3ϕ into co-cultures that contained the same mutagen and 100% target-host with the natural infectivity cycle under mutagenic stress across pure host cultures and how phage populations show simple dilution loss between passages with no recovery according to an embodiment of the disclosure.

FIGS. 18A-18D compares the resulting phage titers from each passage through cultures containing 100% host to those containing 100% target-host, assayed against original host. FIGS. 18A and 18B compare the resulting concentrations of each phage type under null mutagen conditions and depict a decline in target-host samples by simple dilution incurred from passaging. FIGS. 18C and 18D compare them under mutagenic stress and show a decline followed by a phage population rebound in B1 but not in B3.

The steady decline in phage populations seen in cultures containing only the target-host drops incrementally in correlation to the inherent dilution that accompanies passaging them from culture to culture. The phage population that is introduced into a culture where it has nothing to infect has no opportunity replicate and therefore no opportunity to mutate in such a way as to cause them to undergo a host expansion event (see FIGS. 18A-18D). As seen in FIGS. 15A-15D, 16A-16D and 17A-17D, the trends followed by phage populations passaged across 100% original-host cultures as seen in 14A-14D are similar to the trends seen in the phage populations passaged across their corresponding co-cultures. Since naïve bacterial cells were used for each passaging event, the phage populations themselves were the only component to have participated in each passage; yet the trends are obviously similar between the two culture motifs. More, the phage populations that were passaged along each ratio of host and target-host co-cultures were independent from one another yet they still followed similar growth cycles as their cohort populations.

Both B1 and B3 phage concentrations increased dramatically in co-cultures containing 50% or greater concentration of the host organism. They also gained infective activity to the target-host either comparable or greater to that of the host (see FIGS. 14A-14D and 15A-15D). In contrast, a decrease in host-infecting phage concentrations was shown in co-cultures containing 50% or less host in the co-cultures. Phage propagation in 100% host cultures sharply increased upon the first passage, declined to near zero through passages 2-4, increased to over 15-times the starting phage titer, and then dropped again after the sixth passage. In the presence of MC, however, B1 concentrations sharply increased to 22-times from where it started and then dropped to a concentration comparable to the starting concentrations (see FIGS. 15A-15D). Cultures devoid of MC, that included 90% host, increased in phage concentration after the first round of infection, waned after the second passage, fell below the starting concentration over two passages, and rebounded to concentrations above the starting titer through the last two passages. With MC present, B1 phage titers followed the same trend but had markedly higher concentrations in later passages (see FIGS. 16A-16D). The large spike seen in the fifth passage of B1 +MC could be due to a population rebound caused by a bacterial resistance to MC in that specific culture. Bacterial resistance could cause more bacterial growth, causing more phage propagation, resulting in the larger phage population seen in FIGS. 4A-4D. Since, all the bacteria that could have acquired a resistance to the phage from that round were removed and replaced with a new bacterial culture, naïve to the phage, the resulting bacterial culture would be expected to decline, as was seen in the following passage (see FIGS. 17A-17D). B3 did not show increased concentrations as large as B1 did with the host organism (see FIGS. 15A-15D). Though starting with a concentration one order of magnitude higher than that of B1, B3 populations fell below the starting titers in almost every instance. B3 grew to concentrations well above their starting point in −MC infections containing 50% or more of the host organism. B3 populations from +MC conditions only increased in concentration past their starting point in cultures containing 90% host and only after several iterations of co-culture infections.

Figure 19A:
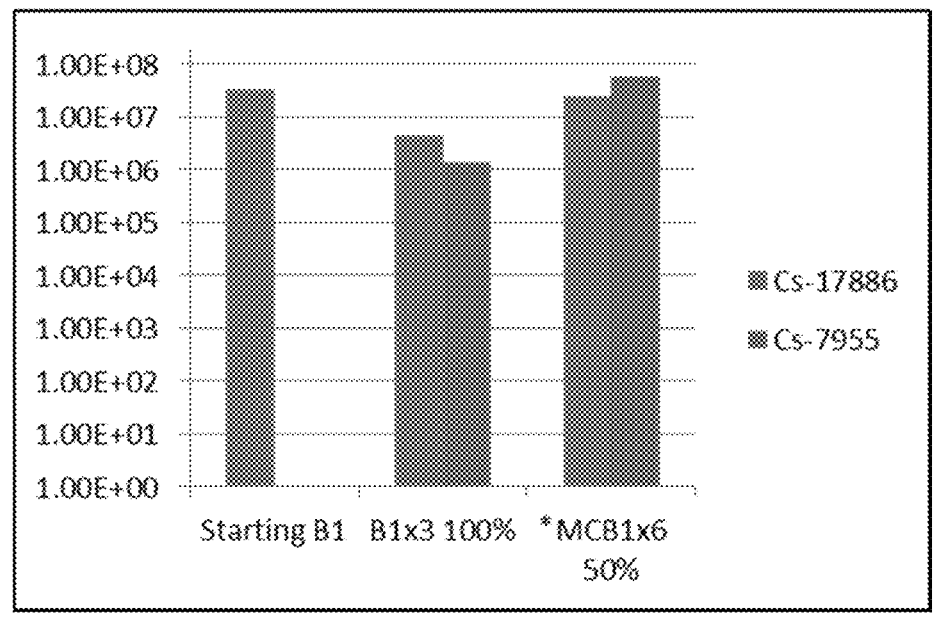
FIG. 19A shows a comparison of B1ϕ population yield between mutagen-added and mutagen-absent conditions propagated in the host and in the target-host. B1 has gained significant infective activity against the target-host without the presence of a mutagen but the mutant phage that was produced maintained infective activity against the host and gained even more infective activity against the target-host according to an embodiment of the disclosure.

FIG. 19A shows a comparison of B1φ population yield between mutagen-added and mutagen-absent conditions propagated in the host and in the target-host. B1 has gained significant infective activity against the target-host without the presence of a mutagen but the mutant phage that was produced maintained infective activity against the host and gained even more infective activity against the target-host.

Figure 19B:
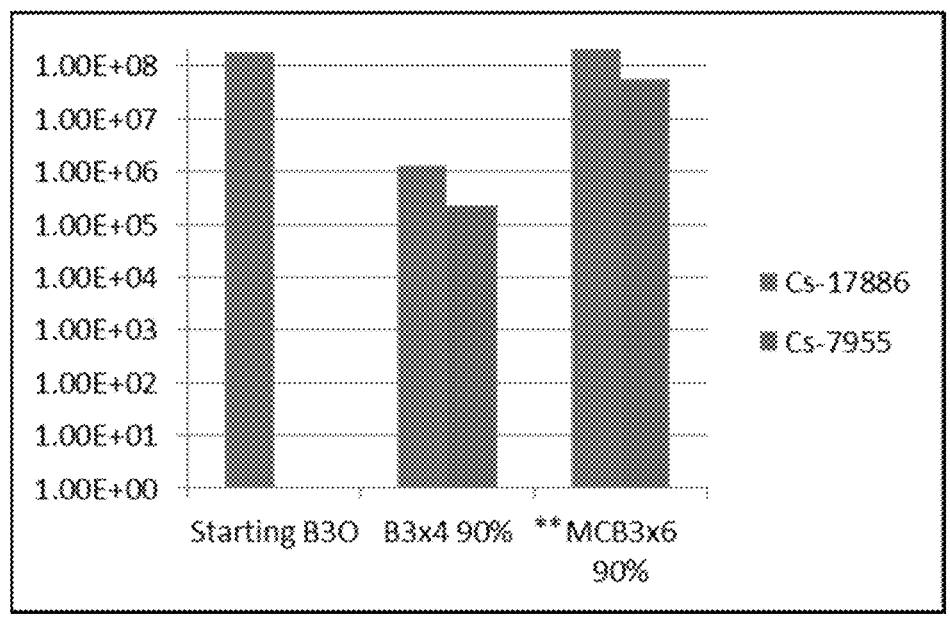
FIG. 19B shows a comparison of B3ϕ population yield between mutagen-added and mutagen-absent conditions propagated in the host and in the target-host. B3 has gained significant infective activity against the target-host without the presence of a mutagen but the mutant phage that was produced maintained infective activity against the host and gained much more infective activity against the target-host under mutagenic stress than without, according to an embodiment of the disclosure.

FIG. 19B shows a comparison of B3φ population yield between mutagen-added and mutagen-absent conditions propagated in the host and in the target-host. B3 has gained significant infective activity against the target-host without the presence of a mutagen but the mutant phage that was produced maintained infective activity against the host and gained much more infective activity against the target-host under mutagenic stress than without.

As can be seen in FIGS. 19A and 19B, B1 lost 86% infecting activity against the host where B3 lost 93%, but each fixed mutant is active against the target-host by 4% and 0.001% of their original activity against the host. In the presence of mutagen, B1 lost 24% infective activity against the host where B3 increased by 10%. B1 gained 65% more infecting activity against the target-host compared to its starting activity against the host organism and B3 gained 30% activity against the target-host. *MCB1×6 50% is the B1 mutant phage derived from the sixth passage in the 50% host: 50% target-host co-culture ratio under mutagenic conditions. **MCB3×6 90% is the B3 mutant phage derived from the sixth passage in 90% host: 10% target-host co-culture ratio under mutagenic conditions.

As can be further seen in FIGS. 19A-19B, comparing the infectivity of each of the four selected mutant phage populations against the host and target-host, B3 from +MC is noted for having lost 93% activity against the host than before the first passage and gaining 0.1% against the target-host. This notwithstanding, the mutant B3 was still able to propagate in 100% target-host culture. Under +MC conditions however, B3 was found to have increased host infection activity 110% to that of its initial host activity and became roughly 250-times that, more infective to the target-host. B1 mutants however, appear to have taken a different path. The infectivity of B1 from −MC fell by 86%, and also fell by 24% under +MC conditions. B1 infectivity to the target-host under −MC conditions was only 4% that of its initial activity against the host but increased to 165% that of target-host activity.

Viruses are known to carry double stranded or single stranded genomes of RNA or DNA (Ackerman, H. W., 2001 & 2011. The B3 genome was isolated and determined to be a single stranded DNA genome as evidenced by the data presented herein.

Table 5 (FIG. 26) shows dsDNA and ssDNA concentrations present in B3 genome isolates before and after enzyme digestions made to eliminate either form of DNA. B3 is likely to have a ssDNA genome.

First, we eliminated the possibility of either genome being RNA. Aliquots of the original phage samples were first analyzed for dsDNA, ssDNA, and RNA using the Invitrogen Qubit® 2.0 Fluorimeter, with its associated DNA and RNA dye-assay kits, to measure the amount of contaminating DNA and RNA was present in the purified phage samples (see Table 6). Aliquots of B1 and B3 were then treated with RNAse in order to eliminate all possible RNA not associated with either of the phages and reanalyzed (see Table 6). The genomes of each were isolated and purified using a ZR Viral DNA/RNA™ kit (cat# D7020) by Zymo Research and analyzed again (see Table 6). RNA was present before phage lysis but absent directly after the RNAse treatment indicating that all of the RNA contaminant was successfully removed. RNA was also absent after the phage genomes were isolated and purified demonstrating that neither the B1 nor B3 genome is RNA-based (Table 6).

Table 6 shows data from Table 5 in a ratio format between amount of ssDNA present in B3 genome isolates to dsDNA.
Table 6. B3 Phage Isolation.

TABLE 6

B3 Phage Isolation.

|  | ssDNA:dsDNA |
|---|---|
| Untreated sample | 8.5 |
| dsDNA and ssDNA digest | 3 |
| Genome Isolation | 6.6 |
| dsDNA digest | 11.8 |
| ssDNA digest | 3.6 |

Since the vast majority of known phage genomes are dsDNA, sequencing under this assumption of both phages was attempted (Ackerman 2011). After obtaining sequence data from B1 but not B3, the B3 genome was suspected to be ssDNA. To compare the genomes of B1 and B3, aliquots of each were treated with DNAse I (New England Biolabs) and analyzed for both dsDNA and ssDNA prior to phage lysis (see Table 4). Contaminating ssDNA and dsDNA were present in both phage samples before treating with DNAse but largely absent after. This suggests the contaminating DNA was successfully eliminated from the purified phage samples (see Table 4). After the phage genomes of the DNAse-treated phage samples were isolated, the concentrations of dsDNA and ssDNA extracted from B1 comparable. With the B1 genome shown to be dsDNA, these results provide a point of comparison for the B3 genome. From the DNA shearing that occurs during the genome isolation process, the presence of ssDNA in the B1 sample should be expected. Three DNA isolation kits were used to isolate DNAse pretreated B3 genome and all agreed that the B3 genome contains >200% ssDNA content than that of dsDNA (see FIGS. 5A-5D). Since ssDNA is known to loop around and anneal to itself over semi-complementary regions of the strand forming regions of dsDNA, seeing dsDNA would be expected for a ssDNA phage genome.

To provide further evidence that the B3 genome is ssDNA, B3 genome isolates were independently digested by endonuclease or exonuclease enzymes to eliminate either dsDNA or ssDNA and then analyzed for the presence of both ssDNA and dsDNA (see Table 5). Purified B3 samples were digested with DNase I to remove DNA not associated with the phage in the purified sample. The presence of both was found in the purified B3 phage before and after the DNase I treatment. B3 isolated genomes were split into two aliquots where one was treated with T7 Endonuclease I, to eliminate dsDNA, and the other treated with Exonuclease T, to eliminate ssDNA. Each sample was then analyzed for ssDNA and dsDNA concentrations (see Table 5).

The purified phage sample contained 8.5 times more ssDNA than dsDNA and dropped to only 3 times more after being treated with DNase I where it remained after the genome isolation (see Table 6. 11.8 times more ssDNA than dsDNA was found in the sample where dsDNA was eliminated and 3.6 times more ssDNA than dsDNA was found in the sample where ssDNA was eliminated (Table 6). Assuming that many phages within a population make new genetic material but fail to assemble properly and that many phages may simply fall apart and release their genomes for one reason or another, a large amount of phage genome is expected to be present within the purified culture.

Figure 20A:
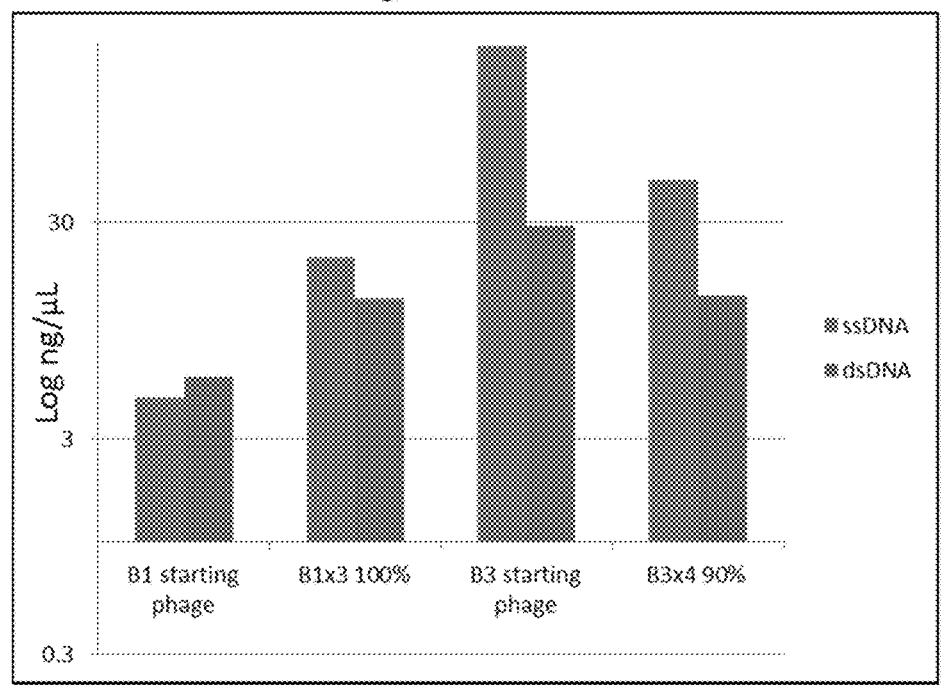
FIG. 20A shows a comparison between the DNA genomes that were isolated from the initial phage strains of B1 and B3 and two mutant phage strains of B1 and B3 that were passaged and propagated under null mutagen conditions. The B1 genome is known to be comprised of dsDNA and its sequence has been published. The B1 genome was used as a benchmark to compare the isolated genomes of the B3 phage types. Where the amounts of ssDNA and dsDNA are comparable in both the B1 phage variants, both B3 variants contained several orders of magnitude more ssDNA than dsDNA suggesting that the B3 phage types contain a ssDNA genome.

FIG. 20A shows both B1 gDNA isolations resulted in very little difference between ssDNA and dsDNA concentrations where in both isolations from B3 reflect the presence of much more ssDNA than dsDNA.

Figure 20B:
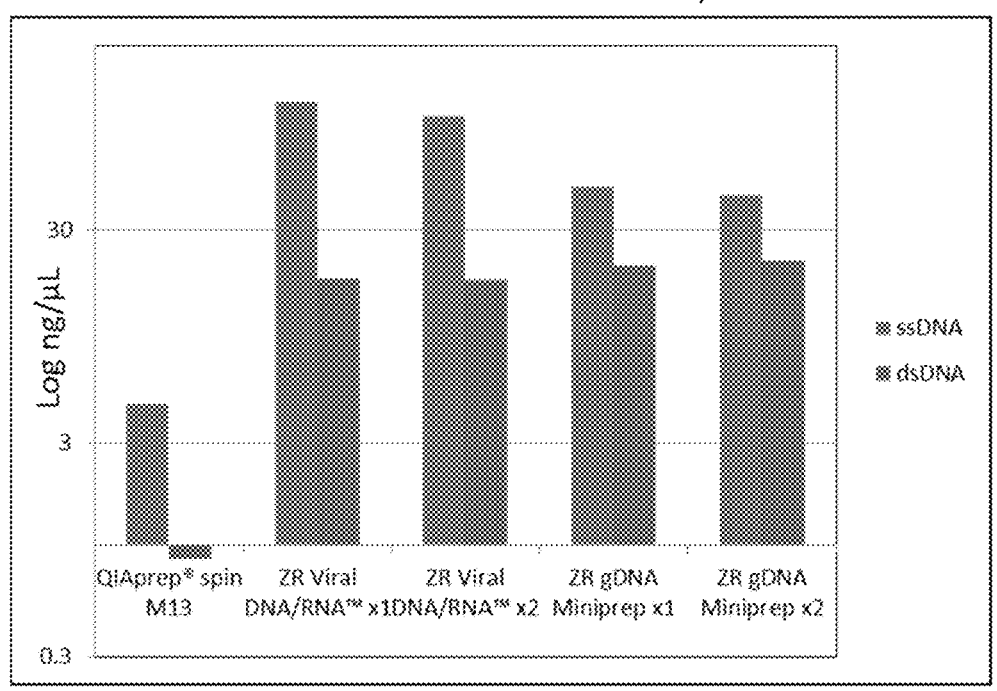
FIG. 20B shows a comparison of the dsDNA and ssDNA concentrations extracted from the B3 genome using different DNA purification kits. Though the total amounts of ssDNA and dsDNA that were isolated by each kit vary, in every instance there were several orders of magnitude more ssDNA isolated than dsDNA which further supports the possibility that the B3 genome is comprised of ssDNA and not dsDNA.

FIG. 20B shows DNA isolations from B3 using three different kits all showing many more times more ssDNA present that dsDNA with a significantly larger yield from the ZR Viral DNA/RNA™ kit from both reactions that were run.

FIGS. 20A and 20B offer compelling evidence that the genome of the B3 phage is comprised of ssDNA.

Figure 21:
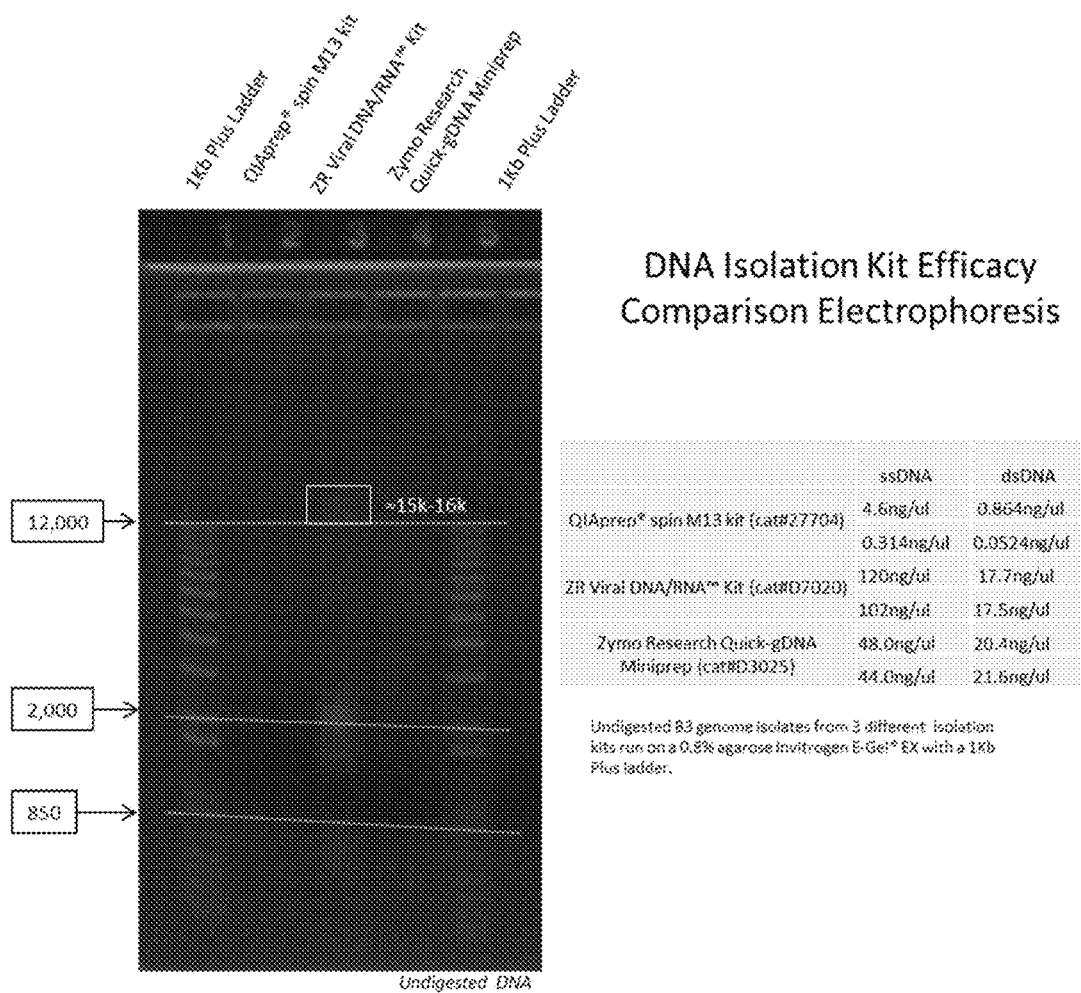
FIG. 21 shows an electrophoresis gel that includes the genome isolations from the B3 phage depicted in FIG. 20B compared to a 1 KB ladder for scale. A table that includes the corresponding ssDNA and dsDNA yields from each extraction kit is included to reference the bands seen in each lane of the gel. Though it is not known if the B3 genome is comprised of circular or linear ssDNA, this gel shows that the B3 genome is at least 15 kb long.

FIG. 21 shows an electrophoresis gel that includes the genome isolations from the B3 phage depicted in FIG. 20B compared to a 1 KB ladder for scale. A table that includes the corresponding ssDNA and dsDNA yields from each extraction kit is included to reference the bands seen in each lane of the gel. Though it is not known if the B3 genome is comprised of circular or linear ssDNA, this gel shows that the B3 genome is at least 15 kb long.

Phage genome size was also estimated prior to attempts to sequence them through gel electrophoresis. The B3 genome isolates from the three DNA isolation kits were compared using the Invitrogen Qubit® 2.0 Fluorometer and an 0.8% agarose E-Gel® EX electrophoresis Kit (see FIG. 21). In addition to estimating genome sizes this also helped to determine the from the ZR Viral DNA/RNA™ Kit and gel electrophoresis shows a sharp band at roughly 14-15 kb along with small fragments of DNA or RNA (see FIG. 21). It is yet to be determined if the genomes of either phage are circular or linear and since no attempt was made to enzymatically linearize either, the 14-15 kb genome length seen in FIG. 21 should only be viewed as an estimated genome size. Since DNA also exists in a supercoiled state, these genomes could be circular and supercoiled and so these data only show that each genome is larger than 14 kb. After receiving the sequence data from the B1 genome and learning that the Cs-17886-B1 phage is the same phage as the previously sequenced Cs-8074-B1 phage, the genome size of the B1 here is 47,595-bp long (Mayer et. al 2012). Considering the known B1 genome size and the similarity of the electrophoresis data between B3 and B1, the B3 genome could also be between 14 k and 47 k-b long as well.

Discussion

To investigate the nature of the specific mutations that occurred in each of the two phages, the genomes of the B1 and B3 phages were further examined. Since viruses in general are known to carry either single strand or double strand, RNA or DNA, it was necessary to determine the genome type of each phage first. After eliminating the possibility of an RNA genome for each, it was assumed that they would both carry a dsDNA genome as does the vast majority of all known phages. Sequencing was attempted based on this assumption. After receiving large areas of the B1 genome sequence they were searched in BLAST and determined to be the same sequence as the *C. sporogenes* ATCC 8074-B1 phage which is commercially offered as a phage separate from ATCC 17886-B1.

Since the B3 genome isolation was treated as though it was dsDNA and no sequence data was generated, further investigation into its genome type was initiated. With this outcome along with having already eliminated RNA as a genome possibility, we suspected the B3 genome to be ssDNA. Upon comparing data from the known B1 dsDNA genome and the suspected ssDNA B3 genome it was found that large differences in the quantity of ssDNA vs. dsDNA between their genome isolates (see FIGS. 19A and 19B). Comparable amounts of ssDNA and dsDNA was found in B1 genome isolations but markedly more ssDNA than dsDNA was found in that of B3. This not only supports the idea that the B3 genome is ssDNA but also could help explain why B3 produced more total mutants and why more B3 mutants were able to be fixed. This difference in genome makeup could also help explain why B3 was able to gain infectivity in the host where B1 did not and why B3 was able to become more active in the target-host, by orders of magnitude, than it started against its original host.

The present disclosure shows that the passage of phages across co-cultures of host strains generated mutants that had achieved host-range expansion into a target-host (see Table 1). Some but not all of these mutant phage populations were able to be propagated on the target-host in a plaque assay. The inability of many of the mutants to productively infect the target-host, speaks to the variance in their stability. Since many mutants were not able to persist in a culture containing 100% target-host and others were able to thrive, perhaps many different mutations routinely occur, some causing efficient host expansion and others not. Additionally, in the –MC co-culture infections, host expanding mutations did not correlate to the number of passages they underwent but did show a minor correlation to the presence of small concentrations of target-host within the co-cultures used in passaging. Mutations leading to host expansion appeared to have occurred largely at random. To support this, host expanding mutations were found to occur in culture passages that contained no target-host at all. With no impetus to drive such a mutation, clearly these mutations occurred randomly but were simply discovered by screening against the desired target-host. This suggests that many different types of mutations occur at random but the desired mutations seem to occur with higher frequency in co-cultures containing at least 10% target-host. With a wealth of natural host available, more phage propagation is able to occur providing more opportunities for mutation. With the addition of the target-host, it then would be readily available within the co-culture to propagate those phages which happened to mutate in such a way as to infect the target-host. By adding MC to the co-culture a higher number of initially productive mutations occur in co-cultures containing a small amount of target-host (see Table 2). The +MC experiments also had more overall mutations when compared to −MC experiments. The likelihood that the genome of B3 is ssDNA a plausible explanation for why we see more mutations for B3 than for B1 since ssDNA is less stable than dsDNA and more prone to mutation. Many productive mutations were routinely seen through passaging but more were seen in infections with an added mutagen and a small amount of the target-host. The mutagen causes a higher frequency of overall mutation and the presence of the target-host helps propagate the mutant phages that happen to be able to infect them.

Harvesting plaques harboring the desired host expansion mutations presents a problem. Each individual plaque forming unit could conceivably represent a unique mutation event within the phage genome, indeed many genetically unique phage variants could exist within a single plaque. By treating the plaques in each assay as a Single Productive Mutation (SPM) however, and placing them in culture containing 100% target-host, each phage variant must compete for survival and to dominate the phage population. Out of this competition, comes a consensus population of the mutant phages that carry the mutations which caused them to out-compete the other mutant phages within the same environment.

Of the 28 phage mutants discovered, only six were able to propagate in 100% target-host culture. Four of the six fixed mutants were selected to represent both phage-types under both +MC and −MC conditions. It is worth noting that almost twice the mutations for each phage type (B1 and B3) were seen under +MC conditions than in the absence of a mutagen. This further indicates that the addition of MC speeds the host-expansion process for phages. Further, in both environments, the B3 phage represented over 130-260% more fleeting mutants than the B1 phage, illustrating a dramatic mutation rate difference between the two phage types. In other words, B1 mutates less often than the B3 phage, probably due to its more stable dsDNA genome. This may indicate that phage-types with ssDNA genomes may be more prone to directed host expansion than others with dsDNA, making them better candidates for industrial use.

The phage product from each co-culture infection was titer assayed to determine the concentration of phage present that infects the original host. The populations of phage naïve to the target-host and only ever passaged in cultures containing 100% original host, increased and decreased in a cyclic pattern (see FIG. 14A-14D). This fluctuation was used as a standard cycle of growth and attrition to compare the growth changes in the co-culture infections against. All of the phage populations being passaged between the co-culture environments followed the same cyclic trend, with the exception of the culture containing 100% target-host (see FIGS. 14A-14D, 15A-15D, 16A-16D, 17A-17D and 18A-18D). Since phage populations were assigned to be passaged through only one co-culture ratio, the growth fluctuations seen in each population is truly separate from the others. Still, the growth cycles seen in each phage population follow the same growth cycle trend as the phage propagated in 100% original host culture. Since the growth cycles for each phage population is independent of one another, the fact that they are all similar to one another is a reproducible phenomenon and can be used as a tool for comparing the overall infectivity across mutant phage populations.

In comparing the growth patterns for both phage populations, it is clear that passaging phage in cultures containing a small percentage of target-host causes the overall phage population to remain higher than without the presence of the target-host. As the target-host percentage increases in the co-culture however, the overall phage population declines to nothing more than a simple dilution curve as seen in those passages across cultures containing 100% target-host (see FIG. 18A-18D). It should be noted that all of the growth fluctuation patterns seen in the co-culture infections of B3 −MC are different than those of B1 and B3 in the +MC experiments and B1 in the −MC experiments (see FIGS. 14A-14D, 15A-15D, 16A-16D and 17A-17D). Where passages 3 and 4 in the B3 −MC experiments show an increasing population trend, all of the others show a decreasing population trend. If the addition of the mutagen caused this growth cycle phase-shift in B3, it clearly did not cause the same result in the B1 phage populations. In contrast, B3 propagated in 100% target-host, phage populations under both conditions where simply diluted out by passaging (see FIGS. 18A-18D). The same trend was shown for B1 under −MC conditions but no dilution curve is seen for B1 populations in the +MC conditions. Though this trend is indicative of a rebounding population of phages that could have undergone host expansion, they went undetected in the initial screening where only 1% of each phage product volume was screened against the target-host and therefore went unrecorded in this study. Still, if the addition of the mutagen caused this phage population rebound, it failed to do the same for both phage types. It should also be noted that that the sinusoidal B3 population cycles from each co-culture ratio under the −MC condition appears to be completely out of phase relative to those of the B3 from +MC for all of the co-culture ratios except one. The exception is in the B3 growth cycle form co-culture infections containing 90% target-host which appears to be more similar to the growth cycles found in the B3+MC experiments (see FIG. 17A-17D).

In an embodiment, phages produced by the disclosed method may be applied against a broad range of bacteria as a treatment, disinfectant and/or decontaminant. In an embodiment, phages created the disclosed method may be applied against nosocomial infections. In an embodiment, the bacteriophages produced by the disclosed method may be applied against, infections acquired to dental work and the bacterial decontamination of the equipment used in these fields.

In an embodiment, phages produced by the disclosed method may be used against, but not limited to, the following bacterial organisms listed here:

Bacillus cereus
Streptococcus pneumoniae
Candida albicans
Multi Drug Resistant *Pseudomonas aeruginosa*
Acinetobacter baumannii
Stenotrophomonas maltophilia
*Clostridium difficile*
*Clostridium novyi*
*Clostridium septicum*
*Clostridium histolyticum*
*Clostridium bifermentans*
*Clostridium sporogenes*
Legionella pneumonia
Listeria monocytogenes Bacterial infections typically found in developing countries (in addition to what is listed above)
Shigella dysenteriae
Cryptosporidiosis/Cryptosporidium
Giardia lamblia
Giardia duodenalis Common bacteria that can lead to necrotizing fasciitis can be targeted for phage attack also include:
Streptococcus pyogenes
(Methicillin resistant) *Staphylococcus aureus* (MRSA)
*Clostridium perfringens*
Bacteroides fragilis
Aeromonas hydrophila Common bacterial agents which impact livestock productions include: Multi Drug Resistant *Pseudomonas aeruginosa*
Salmonella typhimurium
Salmonella dublin
Escherichia coli
"Blackleg"—*Clostridium chauvoei*
"Black Disease"—*Clostridium novyi*
*Clostridium septicum*
*Clostridium chauvoei*
*Clostridium perfringens*
*Clostridium sordellii*
*Clostridium haemolyticum*
Brucella abortus—cows and humans
Leptospira—cows
Trichomonas vaginalis—cow/human STD
Cryptosporidiosis/Cryptosporidium
Vibrio cholerae
Tubercle bacillus—cows
*Moraxella bovis* (bovine pinkeye)
Biothreats
*Bacillus anthracis* (Anthrax)
*Yersinia pestis* (bubonic plague)
Francisella tularensis
*Clostridium botulinum*
Burkholderia mallei
Coxiella burnetii
Rickettsia prowazekii While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. A method of producing bacteriophages with expanded host-range, comprising:
   determine that a selected phage strain infects a host bacterial strain and not a target-host bacterial strain, wherein the selected phage strain is a *Clostridium sporogenes* B1 phage or a *Clostridium sporogenes* B3 phage, the host bacterial strain is a first *Clostridium sporogenes* strain, and the target-host bacterial strain is a second *Clostridium sporogenes* strain;
   culture the host bacterial strain and the target-host bacterial strain separately to obtain a host culture and a target-host culture, respectively;
   mix the host culture and the target-host culture into various co-culture ratios of each, thereby obtaining a series of a plurality of first co-cultures;
   add the selected phage strain to each of the plurality of first co-cultures;
   add a predetermined mutagen to each of the plurality of first co-cultures, wherein the predetermined mutagen comprises mitomycin C;
   incubate under bacterial culture conditions;
   harvest a resulting phage from each of the plurality of first co-cultures and purify; and
   apply the resulting phage to a subsequent set of co-cultures identical to the first co-cultures but naive to the phage.

2. A method of producing bacteriophages with expanded host-range, comprising:
   determine that a selected phage strain infects a host bacterial strain and not a target-host bacterial strain, wherein the selected phage strain is a *Clostridium sporogenes* B1 phage or a *Clostridium sporogenes* B3 phage, the host bacterial strain is a first *Clostridium sporogenes* strain, and the target-host bacterial strain is a second *Clostridium sporogenes* strain;

subject the selected phage in bacterial co-cultures consisting of various ratios of the host bacterial strain and the target-host bacterial strain;

separate the host bacterial strain, the target-host bacterial strain, and a resulting phage;

assay the resulting phage against naïve host and target-host to determine if a host-expansion event has occurred;

repeat phage purification, passaging, and assaying for host-expansion into target-host until there is evidence of infecting activity against target-host bacterial strain; and isolate a mutant phage and cultivate in naïve target-host culture to produce a population of phage mutant.

3. The method of claim 2, further comprising:

combining one or more populations of mutant phages to produce a mutant phage cocktail.

4. The method of claim 1, wherein the series of the plurality of first co-cultures comprises a ratio of 1:0, 9:1, 1:1, 1:9, and 0:1 of the host bacterial strain:the target-host bacterial strain.

5. The method of claim 1, wherein the incubate step is performed under static, anaerobic conditions.

6. The method of claim 1, wherein the resulting phage is a mutant phage comprising ssDNA genome.

7. The method of claim 1, further comprising, after the apply step:

isolate the resulting phage; and ensure the resulting phage infects the target-host bacterial strain, thereby identifying a host-expanded mutant phage.

8. The method of claim 7, further comprising, after the ensure step:

propagate further the host-expanded mutant phage in a target-host culture.

9. The method of claim 1, further comprising, after the apply step:

passaging the resulting phage cultivated in each co-culture ratio.

10. The method of claim 2, wherein the bacterial co-cultures comprises a ratio of 1:0, 9:1, 1:1, 1:9, and 0:1 of the host bacterial strain:the target-host bacterial strain.

11. The method of claim 2, wherein the subject step is performed under static, anaerobic conditions.

12. The method of claim 2, wherein the mutant phage comprises ssDNA genome.

13. The method of claim 2, further comprising, after the isolate step:

propagate further the mutant phage in a target-host culture.

* * * * *